(12) United States Patent
Forte et al.

(10) Patent No.: US 8,394,763 B2
(45) Date of Patent: Mar. 12, 2013

(54) CYCLIC UNDECAPEPTIDES AND DERIVATIVES AS MULTIPLE SCLEROSIS THERAPIES

(75) Inventors: Michael Forte, Portland, OR (US); Dennis Bourdette, Portland, OR (US); Gail Marracci, Scappoose, OR (US)

(73) Assignees: Oregon Health & Science University, Portland, OR (US); The United States of America as represented by the Department of Veterans Affairs, Washington, DC (US)

( * ) Notice: Subject to any disclaimer, the term of this patent is extended or adjusted under 35 U.S.C. 154(b) by 282 days.

(21) Appl. No.: 12/679,778

(22) PCT Filed: Sep. 26, 2008

(86) PCT No.: PCT/US2008/077910
§ 371 (c)(1),
(2), (4) Date: Mar. 24, 2010

(87) PCT Pub. No.: WO2009/042892
PCT Pub. Date: Apr. 2, 2009

(65) Prior Publication Data
US 2010/0196317 A1    Aug. 5, 2010

Related U.S. Application Data

(60) Provisional application No. 60/975,502, filed on Sep. 26, 2007.

(51) Int. Cl.
| | |
|---|---|
| *A01N 37/18* | (2006.01) |
| *A61K 38/04* | (2006.01) |
| *A61K 38/12* | (2006.01) |
| *A61K 38/00* | (2006.01) |
| *A61P 31/04* | (2006.01) |
| *C07K 14/575* | (2006.01) |

(52) U.S. Cl. .................. 514/2.9; 514/2.4; 514/17.9
(58) Field of Classification Search .................. None
See application file for complete search history.

(56) References Cited

U.S. PATENT DOCUMENTS

| | | | | |
|---|---|---|---|---|
| 4,883,666 | A * | 11/1989 | Sabel et al. | ............... 424/422 |
| 5,767,069 | A * | 6/1998 | Ko et al. | ............... 514/20.5 |
| 5,981,479 | A | 11/1999 | Ko et al. | |
| 6,051,596 | A * | 4/2000 | Badger | ............... 514/409 |
| 6,316,405 | B1 | 11/2001 | Rich et al. | |
| 6,444,643 | B1 | 9/2002 | Steiner et al. | |
| 6,927,208 | B1 | 8/2005 | Wenger et al. | |
| 6,995,139 | B2 | 2/2006 | Wenger et al. | |
| 2003/0104992 | A1 | 6/2003 | Or et al. | |
| 2006/0069016 | A1 | 3/2006 | Molino et al. | |

FOREIGN PATENT DOCUMENTS

| | | |
|---|---|---|
| BE | 895 724 | 7/1983 |
| EP | 0 365 044 | 4/1990 |
| WO | WO 2005/097116 | 10/2005 |
| WO | WO 2006/038088 | 4/2006 |

OTHER PUBLICATIONS

Trapp et al. Axonal Transection in the Lesiom of Multiple Sclerosis. The New England Journal of Medicine. 1998, vol. 338, pp. 278-285.*
Thompson et al. Major Differences in the Dynamics of Primary and Secondary Progressive Multiple Sclerosis, Ann. Neurol, 1991, 29, pp. 53-62.*
Clarke et al., "Sanglifehrin A Acts as a Potent Inhibitor of the Mitochondrial Permeability Transition and Reperfusion Injury of the Heart by Binding to Cyclophilin-D at a Different Site from Cyclosporin A," *The Journal of Biological Chemistry*, vol. 277, No. 38, pp. 34793-34799, 2002.
El Rouby et al., "Comparison of the properties of the CsA analogs monoacetyl CyC (*o*-acetyl-threonine$^2$ cyclosporin) and methylalanyl CsA (N-methyl-L-alanyl$^6$ cyclosporin); monoacetyl cyclosporine is immunosuppressive without binding to cyclophilin," *Clin. Exp. Immunol.*, vol. 89, pp. 136-142, 1992.
Forte et al., "Cyclophilin D inactivation protects axons in experimental autoimmune encephalomyelitis, an animal model of multiple sclerosis," *PNAS*, vol. 104, No. 18, pp. 7558-7563, 2007.
Paeshuyse et al., "The Non-Immunosuppressive Cyclosporin DEBIO-025 Is a Potent Inhibitor of Hepatitis C Virus Replication In Vitro," *Hepatology*, vol. 43, No. 4, pp. 761-770, 2006.
Ptak et al., "Inhibition of Human Immunodeficiency Virus Type 1 Replication in Human Cells by Debio-025, a Novel Cyclophilin Binding Agent," *Antimicrobial Agents and Chemotherapy*, vol. 52, No. 4, pp. 1302-1317, 2008.
Skotnicki and Huryn, "Treatment of Transplantation Rejection and Multiple Sclerosis," *Comprehensive Medicinal Chemistry II*, vol. 7, pp. 917-932, 2007.
Steyn et al., "A Double-Blind Placebo-Controlled Study in HIV-1-infected Subjects on the Safety, Pharmacokinetics and Antiviral Effect of Cyclophilin A Targeting DEBIO-025," *Conference on Retroviruses & Opportunistic Infection*, Denver, CO, Feb. 5-8, 2006, www.retroconference.org/2006/PDFs/516.pdf.
Waldmeier et al., "Cyclophilin D as a Drug Target," *Current Medicinal Chemistry*, vol. 10, pp. 1485-1506, 2003.

* cited by examiner

*Primary Examiner* — Marcela M Cordero Garcia
(74) *Attorney, Agent, or Firm* — Klarquist Sparkman, LLP.

(57) ABSTRACT

A method for treating a subject with multiple sclerosis is disclosed herein. In one embodiment, a method is provided for treating a subject with multiple sclerosis that includes administering to the subject a therapeutically effective amount of a cyclosporin compound.

12 Claims, 10 Drawing Sheets

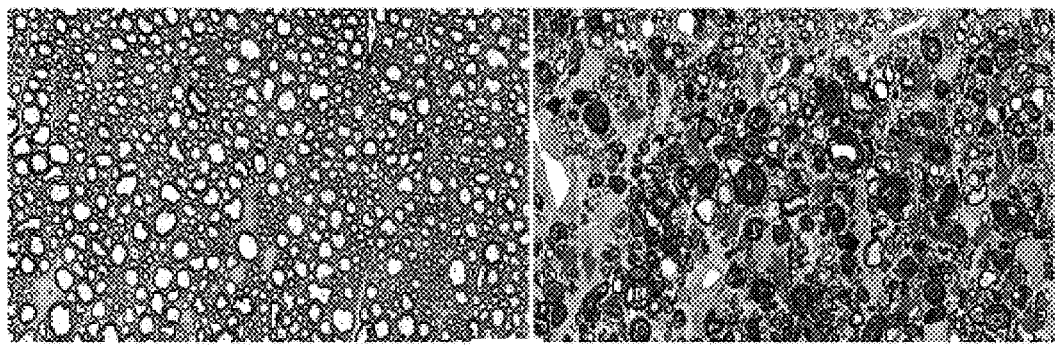
FIG. 4A
FIG. 4B
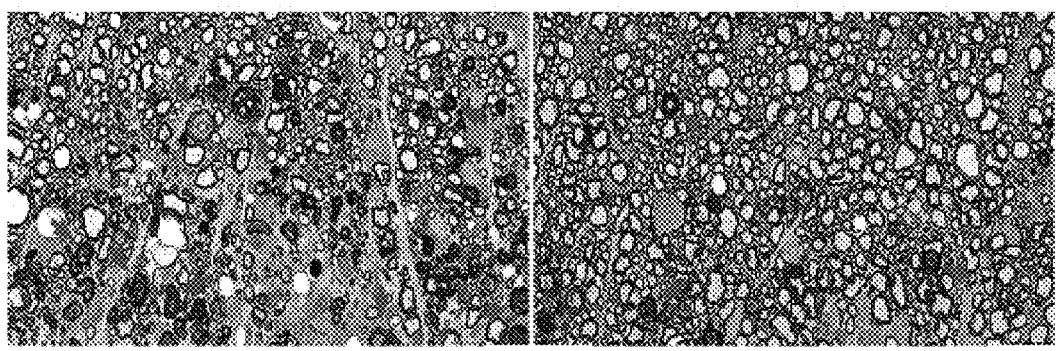
FIG. 4C
FIG. 4D
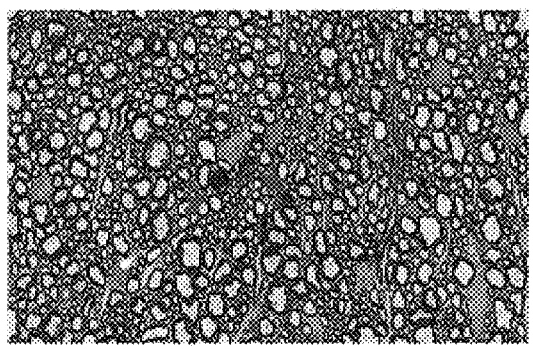

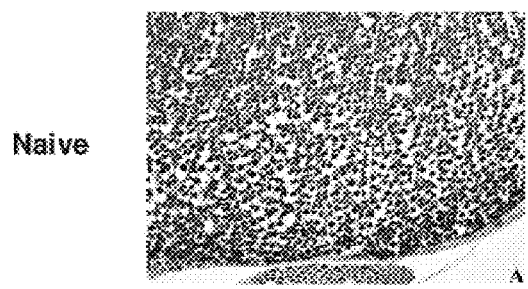
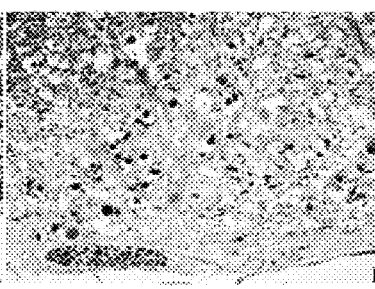
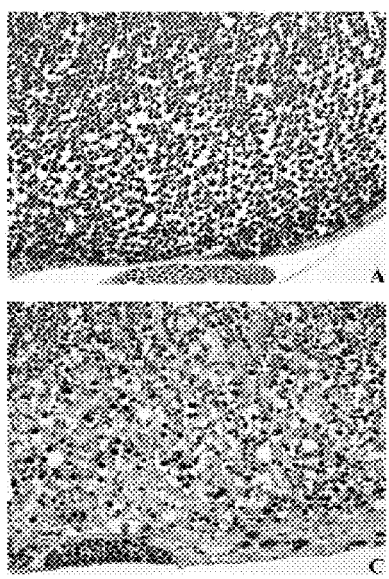
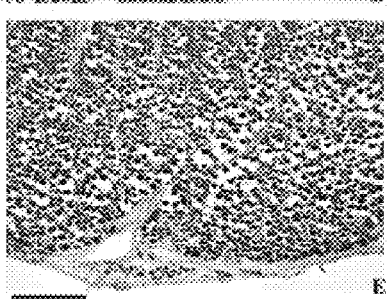
FIG. 5A  FIG. 5B  FIG. 5C  FIG. 5D  FIG. 5E

NO TX

VC

[D-MeAla]³
[EtVal]⁴-CsA

NAIVE

NO TX

VC

[D-MeAla]³
[EtVal]⁴-CsA

NAIVE

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial Sequence
<220> FEATURE:
<223> OTHER INFORMATION: Cyclosporin formula 1
<220> FEATURE:
<221> NAME/KEY: MISC_FEATURE
<222> LOCATION: (1)..(1)
<223> OTHER INFORMATION: Xaa is N-methyl-(4R)-4-but-2E-en-1-yl-4-methyl-
      (L)threonine; dihydro-N-methyl-(4R)-4-but-2E-en-1-yl-4-methyl-
      (L)threonine; or 8'-hydroxy-N-methyl-(4R)-4-but-2E-en-1-yl-4-
      methyl-(L)threonine
<220> FEATURE:
<221> NAME/KEY: MISC_FEATURE
<222> LOCATION: (2)..(2)
<223> OTHER INFORMATION: Xaa is alpha-aminobutyric acid; Val, Thr,
      norvaline, or O-methylthreonine
<220> FEATURE:
<221> NAME/KEY: MISC_FEATURE
<222> LOCATION: (3)..(3)
<223> OTHER INFORMATION: Xaa is sarcosine, (D)-N-methylserine, (D)-N-
      methylalanine, or (D)-N-methylserine(Oacetyl)
<220> FEATURE:
<221> NAME/KEY: MISC_FEATURE
```

```
<222> LOCATION: (4)..(4)
<223> OTHER INFORMATION: Xaa is N-methylleucine, gamma-hydroxy-N-
      methylleucine, MeIle, MeVal, N-methylthreonine, N-methylalanine,
      allo-MeIle, allo-N-methylthreonine, N-ethylisoleucine,
      N-ethylthreonine, N-ethylphenylalanine, N-ethyltyrosine, or
<220> FEATURE:
<221> NAME/KEY: MISC_FEATURE
<222> LOCATION: (5)..(5)
<223> OTHER INFORMATION: Xaa is Val, Leu, N-methylvaline, or N-
      methylleucine
<220> FEATURE:
<221> NAME/KEY: MISC_FEATURE
<222> LOCATION: (6)..(6)
<223> OTHER INFORMATION: Xaa is N-methylleucine, gamma-hydroxy-N-
      methylleucine, or N-methylalanine
<220> FEATURE:
<221> NAME/KEY: MISC_FEATURE
<222> LOCATION: (8)..(8)
<223> OTHER INFORMATION: Xaa is D-alanine
<220> FEATURE:
<221> NAME/KEY: MISC_FEATURE
<222> LOCATION: (9)..(9)
<223> OTHER INFORMATION: Xaa is N-methylleucine
<220> FEATURE:
<221> NAME/KEY: MISC_FEATURE
<222> LOCATION: (10)..(10)
<223> OTHER INFORMATION: Xaa is N-methylleucine
<220> FEATURE:
<221> NAME/KEY: MISC_FEATURE
<222> LOCATION: (11)..(11)
<223> OTHER INFORMATION: Xaa is N-methylvaline

<400> SEQUENCE: 1

Xaa Xaa Xaa Xaa Xaa Xaa Ala Xaa Xaa Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Cyclosporin formula 2
<220> FEATURE:
<221> NAME/KEY: MISC_FEATURE
<222> LOCATION: (1)..(1)
<223> OTHER INFORMATION: Xaa is N-methyl-(4R)-but-2E-en-1-yl-4-
      methyl(L)threonine or 6,7,dihydro-N-methyl-(4R)-but-2E-en-1-yl-4-
      methyl(L)threonine
<220> FEATURE:
<221> NAME/KEY: MISC_FEATURE
<222> LOCATION: (2)..(2)
<223> OTHER INFORMATION: Xaa is alpha-aminobutyric acid, norvaline, Val,
      or Thr
<220> FEATURE:
<221> NAME/KEY: MISC_FEATURE
<222> LOCATION: (3)..(3)
<223> OTHER INFORMATION: Xaa is sarcosine, (D)-N-methylserine, (D)-N-
      methylalanine, or (D)-N-methylserine(Oacyl)
<220> FEATURE:
<221> NAME/KEY: MISC_FEATURE
<222> LOCATION: (4)..(4)
<223> OTHER INFORMATION: Xaa is (N-R)aa where aa={Val, Ile, Thr, Phe,
      Tyr, Thr(OAc), Thr(OG1), Phe(G2), PheCH2(G3), or Tyr(OG3)} with
      R={alkyl>CH3}; G1={phenyl-COOH, phenyl-COOMe, or phenyl-COOEt};
<220> FEATURE:
<221> NAME/KEY: MISC_FEATURE
<222> LOCATION: (6)..(6)
<223> OTHER INFORMATION: Xaa is N-methylleucine
<220> FEATURE:
<221> NAME/KEY: MISC_FEATURE
<222> LOCATION: (8)..(8)
<223> OTHER INFORMATION: Xaa is (D)-alanine
<220> FEATURE:
<221> NAME/KEY: MISC_FEATURE
<222> LOCATION: (9)..(9)
<223> OTHER INFORMATION: Xaa is N-methylleucine
<220> FEATURE:
<221> NAME/KEY: MISC_FEATURE
```

```
<222> LOCATION: (10)..(10)
<223> OTHER INFORMATION: Xaa is N-methylleucine
<220> FEATURE:
<221> NAME/KEY: MISC_FEATURE
<222> LOCATION: (11)..(11)
<223> OTHER INFORMATION: Xaa is N-methylvaline

<400> SEQUENCE: 2

Xaa Xaa Xaa Xaa Val Xaa Ala Xaa Xaa Xaa Xaa
1               5                   10

<210> SEQ ID NO 3
<211> LENGTH: 11
<212> TYPE: PRT
<213> ORGANISM: Tolypocladium inflatum
<220> FEATURE:
<221> NAME/KEY: MISC_FEATURE
<222> LOCATION: (1)..(1)
<223> OTHER INFORMATION: Xaa is N-methyl-(4R)-but-2(E)-en-1-yl-4-methyl-
      (L)-threonine
<220> FEATURE:
<221> NAME/KEY: MISC_FEATURE
<222> LOCATION: (2)..(2)
<223> OTHER INFORMATION: Xaa is alpha-aminobutyric acid
<220> FEATURE:
<221> NAME/KEY: MISC_FEATURE
<222> LOCATION: (3)..(3)
<223> OTHER INFORMATION: Xaa is sarcosine
<220> FEATURE:
<221> NAME/KEY: MISC_FEATURE
<222> LOCATION: (4)..(4)
<223> OTHER INFORMATION: Xaa is N-methylleucine
<220> FEATURE:
<221> NAME/KEY: MISC_FEATURE
<222> LOCATION: (6)..(6)
<223> OTHER INFORMATION: Xaa is N-methylleucine
<220> FEATURE:
<221> NAME/KEY: MISC_FEATURE
<222> LOCATION: (8)..(8)
<223> OTHER INFORMATION: Xaa is (D)-alanine
<220> FEATURE:
<221> NAME/KEY: MISC_FEATURE
<222> LOCATION: (9)..(9)
<223> OTHER INFORMATION: Xaa is N-methylleucine
<220> FEATURE:
<221> NAME/KEY: MISC_FEATURE
<222> LOCATION: (10)..(10)
<223> OTHER INFORMATION: Xaa is N-methylleucine
<220> FEATURE:
<221> NAME/KEY: MISC_FEATURE
<222> LOCATION: (11)..(11)
<223> OTHER INFORMATION: Xaa is N-methylvaline

<400> SEQUENCE: 3

Xaa Xaa Xaa Xaa Val Xaa Ala Xaa Xaa Xaa Xaa
1               5                   10

<210> SEQ ID NO 4
<211> LENGTH: 4
<212> TYPE: PRT
<213> ORGANISM: Artificial Sequence
<220> FEATURE:
<223> OTHER INFORMATION: cyclophilin substrate

<400> SEQUENCE: 4

Ala Ala Pro Phe
1

<210> SEQ ID NO 5
<211> LENGTH: 11
<212> TYPE: PRT
<213> ORGANISM: Artificial Sequence
<220> FEATURE:
<223> OTHER INFORMATION: [D-MeAla]3-[EtVal]4-CsA
```

```
<220> FEATURE:
<221> NAME/KEY: MISC_FEATURE
<222> LOCATION: (1)..(1)
<223> OTHER INFORMATION: Xaa is N-methyl-(4R)-4-but-2E-en-1-yl-4-methyl-
      (L)threonine
<220> FEATURE:
<221> NAME/KEY: MISC_FEATURE
<222> LOCATION: (2)..(2)
<223> OTHER INFORMATION: Xaa is alpha-aminobutyric acid
<220> FEATURE:
<221> NAME/KEY: MISC_FEATURE
<222> LOCATION: (3)..(3)
<223> OTHER INFORMATION: Xaa is (D)-N-methylalanine
<220> FEATURE:
<221> NAME/KEY: MISC_FEATURE
<222> LOCATION: (4)..(4)
<223> OTHER INFORMATION: Xaa is N-ethylvaline
<220> FEATURE:
<221> NAME/KEY: MISC_FEATURE
<222> LOCATION: (6)..(6)
<223> OTHER INFORMATION: Xaa is N-methylleucine
<220> FEATURE:
<221> NAME/KEY: MISC_FEATURE
<222> LOCATION: (8)..(8)
<223> OTHER INFORMATION: Xaa is (D)-alanine
<220> FEATURE:
<221> NAME/KEY: MISC_FEATURE
<222> LOCATION: (9)..(9)
<223> OTHER INFORMATION: Xaa is N-methylleucine
<220> FEATURE:
<221> NAME/KEY: MISC_FEATURE
<222> LOCATION: (10)..(10)
<223> OTHER INFORMATION: Xaa is N-methylleucine
<220> FEATURE:
<221> NAME/KEY: MISC_FEATURE
<222> LOCATION: (11)..(11)
<223> OTHER INFORMATION: Xaa is N-methylvaline

<400> SEQUENCE: 5

Xaa Xaa Xaa Xaa Val Xaa Ala Xaa Xaa Xaa Xaa
1               5                   10
```

CYCLIC UNDECAPEPTIDES AND DERIVATIVES AS MULTIPLE SCLEROSIS THERAPIES

CROSS REFERENCE TO RELATED APPLICATIONS

This is the §371 U.S. National Stage of International Application No. PCT/US2008/077910, filed Sep. 26, 2008, which was published in English under PCT Article 21(2), which in turn claims the benefit of U.S. Provisional Application No. 60/975,502, filed Sep. 26, 2007, which is incorporated by reference herein in its entirety.

ACKNOWLEDGMENT OF GOVERNMENT SUPPORT

This invention was made with United States government support pursuant to grant RO1-GM069883 from the National Institutes of Health, and with funds from the Department of Veterans' Affairs; the United States government has certain rights in the invention.

FIELD

This disclosure relates to the treatment of multiple sclerosis using a compound that inhibits cyclophilin activity and exhibits reduced immunosuppressive activity, such as specific analogs of cyclosporin A.

BACKGROUND

Multiple sclerosis (MS) is a chronic, neurological, autoimmune, demyelinating disease. MS can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. In the United States there are about 250,000 to 400,000 persons with MS, and every week about 200 new cases are diagnosed. Worldwide, MS may affect 2.5 million individuals. Because it is not contagious, which would require U.S. physicians to report new cases, and because symptoms can be difficult to detect, the incidence of disease is only estimated and the actual number of persons with MS could be much higher.

The pathology of MS is characterized by an abnormal immune response directed against the central nervous system. In particular, T-lymphocytes reactive against myelin antigens are believed to initiate an inflammatory response within the central nervous system (CNS). The resultant inflammatory response includes recruited T-lymphocytes, activated macrophages, B-lymphocytes and plasma cells. Soluble mediators released by these inflammatory cells result in demyelination and, to a lesser extent, axonal degeneration. Areas within the CNS in which demyelination and axonal injury have occurred develop an astrocytic scar and these scarred or "sclerotic" areas are referred to as plaques. These lesions appear in scattered locations throughout the brain, optic nerve, and spinal cord. Most subjects recover clinically from individual bouts of demyelination, producing the classic remitting and exacerbating course of the most common form of the disease known as relapsing-remitting multiple sclerosis. Many patients eventually enter a progressive phase of disease, referred to as secondary progressive MS, in which they worsen continually. Some patients do not start with a relapsing-remitting course but have progressive disease from onset; this is referred to as primary progressive MS. In both forms of progressive MS, a progressive degeneration of axons is believed to cause the continuous loss of function.

The status of MS patients can be evaluated by longitudinal, monthly follow-up of magnetic resonance (MRI) activity in the brain of MS patients. MRI offers a unique set of outcome measures for phase I/II clinical trials in small cohorts of patients, and is thus well suited to establish data for proof of principle for novel therapeutic strategies (e.g., see Harris et al., *Ann. Neurol.* 29:548-555, 1991; MacFarland et al., *Ann. Neurol.* 32:758-766, 1992; Stone et al., *Ann. Neurol.* 37:611-619, 1995). There are currently six FDA-approved treatments for MS, three types of IFN-β (the Interferon-B multiple sclerosis study group, *Neurology* 43:655-661, 1993; the IFNB Multiple Sclerosis Study Group; and the University of British Columbia MS/MRI Analysis Group, *Neurology* 45:1277-1285, 1995; Jacobs et al., *Ann. Neurol.* 39:285-294, 1996), a random polymer of four amino acids (glatiramer acetate) (Johnson K P, Group. tCMST, *J. Neurol.* 242:S38, 1995), a chemotherapy drug (mitoxantrone) (Hartung et al. *Lancet* 360:2018-2025, 2003), and a humanized monoclonal antibody, natalizumab, directed against alpha4-integrin (O'Connor et al., *Neurology* 62:2038-2043, 2004 and U.S. Pat. Nos. 6,033,665 and 5,840,299, incorporated herein by reference).

Current therapeutic interventions for MS depend exclusively on modulators of the immune/inflammatory response during disease progression. Cyclosporin A (CsA) is an 11 amino acid cyclic peptide of fungal origin that is currently used clinically as an immunosuppressant due to its inhibition of the protein phosphatase calcineurin. CsA has been shown to reduce tissue injury in experimental autoimmune encephalomyelitis (EAE). However, the toxicity associated with long term CsA use has prevented its use as a treatment for MS. Thus, a need remains for additional agents for treatment of MS.

SUMMARY

Methods are disclosed herein for treating a subject, such as a human subject, with multiple sclerosis.

In several embodiments, a method of treating multiple sclerosis includes administering a therapeutically effective amount of a cyclosporin having the formula:

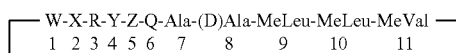

(SEQ ID NO: 1) in which W is MeBmt, dihydro-MeBmt, or 8'-hydroxy-MeBmt;

X is αAbu, Val, Thr, Nva, or O-methyl threonine (MeO-Thr);

R is Sar, (D)-MeSer, (D)-MeAla, or (D)-MeSer(Oacetyl);

Y is MeLeu, γ-hydroxy-MeLeu, MeIle, MeVal, MeThr, MeAla, MeaIle or MeaThr, N-EtVal, N-EtIle, N-EtThr, N-EtPhe, N-EtTyr, or N-EtThr(Oacetyl);

Z is Val, Leu, MeVal, or MeLeu; and

Q is MeLeu, γ-hydroxy-MeLeu, or MeAla, wherein the cyclosporin is not cyclosporin A.

In further embodiments, a method of treating multiple sclerosis includes administering a therapeutically effective amount of a cyclosporin having the formula:

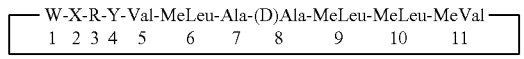
W-X-R-Y-Val-MeLeu-Ala-(D)Ala-MeLeu-MeLeu-MeVal
1  2 3 4 5    6    7   8      9      10    11

(SEQ ID NO: 2) in which W is MeBmt or 6,7-dihydro-MeBmt;

X is αAbu, Nva, Val, or Thr;

R is Sar, (D)-MeSer, (D)-MeAla, or (D)-MeSer(OAcyl);

Y is (N—R)aa where aa={Val, Ile, Thr, Phe, Tyr, Thr(OAc), Thr(OG$_1$), Phe(G$_2$), PheCH$_2$(G$_3$), or Tyr(OG$_3$)} with R={alkyl>CH$_3$};

G$_1$={phenyl-COOH, phenyl-COOMe, or phenyl-COOEt};

G$_2$={CH$_2$COOH, CH$_2$COOMe(Et)$_4$, CH$_2$PO(OMe)$_2$ or CH$_2$PO(OH)$_2$};

G$_3$={PO(OH)$_2$, PO(OCH$_2$CH=CH$_2$)$_2$, CH$_2$COOH, CH$_2$COOMe, or CH$_2$COOEt}, wherein the cyclosporin is not cyclosporin A.

The amino acids described according to their conventional abbreviation have the configuration L unless otherwise specified.

In some embodiments, the cyclosporin is preferably Debio 025 (CAS RN 254435-95-5), which has the chemical name: Cyclo[L-alanyl-D-alanyl-N-methyl-L-leucyl-N-methyl-L-leucyl-N-methyl-L-valyl-(2S,3R,4R,6E)-3-hydroxy-4-methyl-2-methylamino-6-octenoyl-(2S)-2-aminobutanoyl-N-methyl-D-alanyl-N-ethyl-L-valyl-L-valyl-N-methyl-L-leucyl].

In one embodiment, a method is provided for treating a subject with multiple sclerosis, wherein the method includes administering a therapeutically effective amount of a cyclosporin compound described herein at a dose of about 1 mg/kg to about 100 mg/kg. In a further embodiment, the composition is administered once per day.

In an additional embodiment, administration of the cyclosporin compound is combined with administration of a second agent for the treatment of multiple sclerosis.

In several embodiments, the method includes administering to the subject a therapeutically effective amount of a cyclosporin compound that inhibits cyclophilin activity. In a particular embodiment, the method includes administering a therapeutically effective amount of a cyclosporin compound that inhibits cyclophilin D.

The foregoing and other objects, features, and advantages of the invention will become more apparent from the following detailed description, which proceeds with reference to the accompanying figures.

BRIEF DESCRIPTION OF THE DRAWINGS

FIG. 5 shows photomicrographs of thoracic spinal cord sections from C57BL/6 mice immunostained for phosphorylated neurofilaments from (A) Naïve wild type, (B) EAE mouse treated with vehicle alone, (C) mouse with EAE treated with 1 mg/kg/day of [D-MeAla]$^3$[EtVal]$^4$-CsA, (D) mouse with EAE treated with 5 mg/kg/day of [D-MeAla]$^3$[EtVal]$^4$-CsA, (E) mouse with EAE treated with 20 mg/kg/day of [D-MeAla]$^3$[EtVal]$^4$-CsA 40 days after immunization with MOG 35-55 peptide. Bar=50 µm.

FIG. 6 is two schematic diagrams showing percentage of axon damage in thoracic spinal cord. EAE was induced in C57BL/6 mice by immunization with MOG 35-55 peptide. No Tx group is mice which were perfused and assessed for axonal damage on day 15 post-immunization. Vehicle group is mice which received daily injection of vehicle beginning on day 15 post-immunization until termination of the experiment on day 40 post-immunization. [D-MeAla]$^3$[EtVal]$^4$-CsA group is mice which received daily injections of 20 mg/kg [D-MeAla]$^3$[EtVal]$^4$-CsA beginning on day 15 post-immunization until termination of the experiment on day 40 post-immunization.

FIG. 9 shows bar graphs showing the percentage of spinal cord stained for CD4 (left) or CD11b (right) in EAE mice with no treatment (No TX), EAE mice treated with vehicle alone (VC), EAE mice treated with 20 mg/kg/day of

Figure 1:
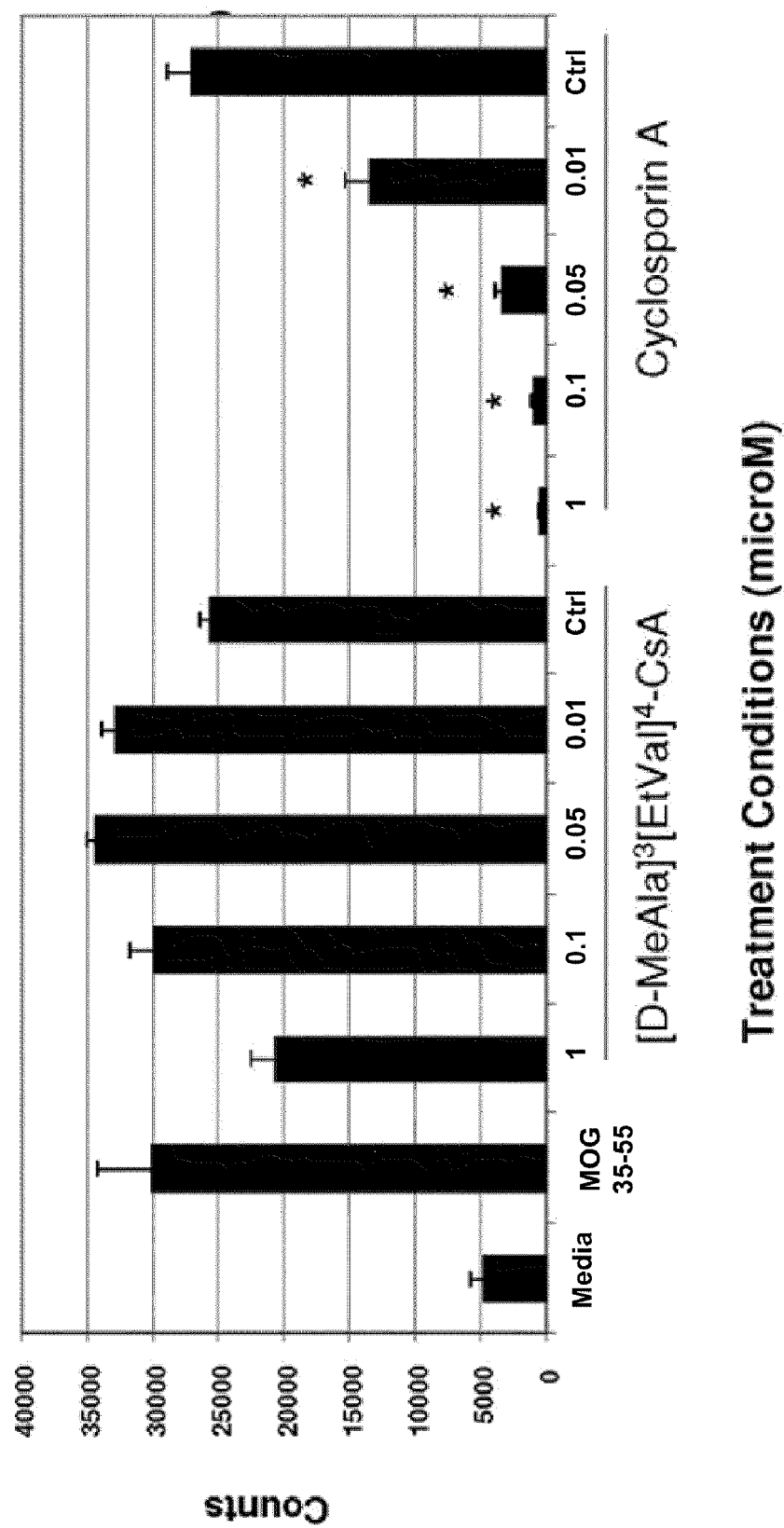
FIG. 1 is a histogram showing mean counts of incorporated [$^3$H]thymidine of lymph node cells isolated from C57BL/6 mice immunized with MOG 35-55 peptide. Triplicate wells of lymph node cells were treated with 25 µg/ml MOG 35-55 peptide in the presence or absence of [D-MeAla]$^3$[EtVal]$^4$-CsA or CsA at the indicated concentrations. Ctrl indicates incubation only with vehicle used to solubilize CsA or [D-MeAla]$^3$[EtVal]$^4$-CsA. Error bars represent standard error of the mean. * indicates a p-value of ≦0.05 (Student's t-test).

[D-MeAla]³[EtVal]⁴-CsA at 34-40 days after immunization with MOG 35-55, and naïve mice.

DETAILED DESCRIPTION

I. Abbreviations
αAbu: L-α-aminobutyric acid
CNS: central nervous system
CsA: cyclosporin A
Cyp: cyclophilin
CypA: cyclophilin A
CypD: cyclophilin D
EAE: experimental autoimmune encephalomyelitis
EDSS: expanded disability status scale
EtIle: N-ethyl-isoleucine
EtPhe: N-ethyl-phenylalanine
EtThr: N-ethyl-threonine
EtTyr: N-ethyl-tyrosine
EtVal: N-ethyl-valine
Gd: gadolinium
IL-2: interleukin-2
MeaIle: allo form of N-methyl-isoleucine
MeaThr: allo form of N-methyl-threonine
MeBmt: N-methyl-(4R)-but-2E-en-1-yl-4-methyl-(L) threonine
MeAla: N-methyl-alanine
MeIle: N-methyl-isoleucine
MeLeu: N-methyl-leucine
MeSer: N-methyl-serine
MeThr: N-methyl-threonine
MeVal: N-methyl-valine
MLR: mixed lymphocyte reaction
MOG: myelin oligodendrocyte glycoprotein
MRI: magnetic resonance imaging
MS: multiple sclerosis
NAA: N-acetyl aspartate
NF-P: neurofilament phosphorylation
Nva: norvaline
PPIase: peptidyl-prolyl cis-trans isomerase
Sar: sarcosine (N-methyl-glycine)
SRS: Scripps Neurological Rating Scale II. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Definitions and additional information known to one of skill in the art in immunology can be found, for example, in *Fundamental Immunology*, W. E. Paul, ed., fourth edition, Lippincott-Raven Publishers, 1999.

In order to facilitate review of the various embodiments of this disclosure, the following explanations of specific terms are provided:

Adverse Effects: Any undesirable signs, including the clinical manifestations of abnormal laboratory results, or medical diagnoses noted by medical personnel, or symptoms reported by the subject that have worsened. Adverse events include, but are not limited to, life-threatening events, an event that prolongs hospitalization, or an event that results in medical or surgical intervention to prevent an undesirable outcome.

Autoimmune disorder: A disorder in which the immune system produces an immune response (e.g. a B cell or a T cell response) against an endogenous antigen, with consequent injury to tissues.

Axon damage: Axon damage includes axon degeneration and a reduction in axon density, for example in the white matter of the caudal spinal cord. White matter tissue damage includes axons undergoing Wallerian-like degeneration, reduced nerve fiber density, and demyelination. White matter tissue damage can be determined by histological examination of white matter, for example from the ventrolateral or dorsal thoracic spinal cord. White matter tissue damage may also be determined by MRI. Evidence of axonal damage can be inferred from presence of abnormal MM signals, such as permanently decreased $T_1$ signals ("black holes"), decreased n-acetyl aspartate (NAA) and whole brain atrophy.

Axon damage also includes decreased neurofilament phosphorylation (NF-P) (see e.g. Trapp et al., *N. Engl. J. Med.* 338:278-285, 1998). Neurofilaments in myelinated axons are normally heavily phosphorylated. NF-P can be determined by immunohistochemical staining. A reduction in NF-P reflects demyelination and axon damage.

Decreasing axon damage in a subject includes a reduction in white matter tissue damage as compared with an untreated subject, such as a reduction in the decrease in NF-P as compared with an untreated subject. Decreasing axon damage also encompasses preventing axon damage and repair of axon damage. Repair of axon damage in a subject includes a reduction in white matter tissue damage or a reduction in the decrease in NF-P as compared with an earlier time point, for example prior to beginning treatment with a cyclosporin compound.

Cyclophilin: Family of proteins having activities of peptidyl-prolyl cis-trans isomerases (PPIase) (EC 5.2.1) that bind to cyclosporins and chaperones.

Cyclophilins A, B, C, D, and cyclophilin-40 have been identified. Cyclophilin A is a 19 kD protein that is expressed in a wide variety of cells. Cyclophilin B is primarily localized to the endoplasmic reticulum of the cell. Cyclophilin C is a 23 kD protein that is primarily cytoplasmic. Cyclophilin D is an 18 kD protein that is encoded by a somatic gene and localized primarily within mitochondria. Cyclophlin-40 is a component of the inactivated form of the glucocorticoid receptor.

Cyclosporin: A structurally distinct class of cyclic poly-N-methylated undecapeptides that bind to cyclophilins. The first cyclosporin isolated was cyclosporin A, which was isolated from a culture of *Tolypocladium inflatum*. Cyclosporin A (CsA) is represented by the formula:

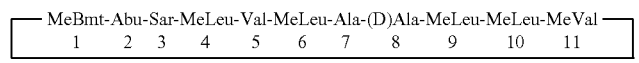

(SEQ ID NO: 3) where MeBmt=N-methyl-(4R)-4-[(E)-2-butenyl]-4-methyl-L-threonine; Abu=L-α-aminobutyric acid; Sar=sarcosine; MeLeu=N-methyl-L-leucine; Val=L-valine; Ala=L-alanine; (D)Ala=D-alanine; and MeVal=N-methyl-L-valine. Since the discovery of cyclosporin A, a large number of other cyclosporins have been identified, as have synthetic or semi-synthetic varieties (see e.g., U.S. Pat. Nos. 6,444,643, and 6,927,208).

CsA binds to and inhibits the PPIase activity of cyclophilins. Cyclophilin PPIase activity can be determined, for example, as in PCT Publication No. WO 06/038088 which is incorporated herein by reference, and can be expressed as a $K_i$. In one example, the cis-trans isomerization of the alanine-proline peptide bond in a model substrate, N-succinyl-Ala-Ala-Pro-Phe-4-nitroanilide (SEQ ID NO: 4), may be monitored spectrophotometrically in a coupled assay with chymotrypsin, which releases 4-nitroanilide from the trans form of the substrate. The inhibitory effect upon the addition of different concentrations of inhibitor on the extent of the reaction is determined, and analysis of the change in the first order rate constant as a function of inhibitor concentration yields an estimate of the apparent $K_i$.

Cyclosporins include cyclosporin compounds which are derivatives or analogs of CsA. In some examples, the cyclosporin compounds have increased inhibitory activity for cyclophilins and/or less or non-immunosuppressant activity as compared to CsA. CsA derivatives include compounds that differ from CsA at any position, such as the cyclosporin compounds described herein. In particular examples, CsA derivatives include compounds that differ from CsA at position 3 which contain an N-methylated, nonbulky hydrophobic or neutral amino acid, such as D-MeSer, D-MeAla, or D-MeSer(OAcyl), particularly D-MeAla. CsA derivatives also include compounds that differ from CsA in position 4, which contain an N-methylated or N-ethylated hydrophobic or neutral amino acid, such as MeIle, MeVal, (4-OH)MeLeu, or EtVal. Other derivatives at position 4 include an amino acid residue of the formula (N—R)aa with R>$CH_3$ and R<$C_{10}H_{21}$. R may be for example, ethyl, propyl, butyl, or pentyl, particularly where the residue in position 4 is an N-ethylated amino acid, particularly N-EtVal. Combinations of derivatives at various positions are also contemplated, for example [D-MeAla]$^3$[EtVal]$^4$-CsA, wherein the compound consists of CsA with the indicated substitutions at positions 3 and 4.

Expanded Disability Status Scale (EDSS): A rating system that is frequently used for classifying and standardizing the condition of people with multiple sclerosis. It is also used to follow the progression of MS disability and evaluate treatment results for similar groupings of people. The EDSS score is a measure of permanent disability in MS. The score is based upon neurological testing and examination of functional systems, which are areas of the central nervous system which control bodily functions. The functional systems are: pyramidal (ability to walk), cerebellar (coordination), brain stem (speech and swallowing), sensory (touch and pain), bowel and bladder function, visual, cerebral, and other (includes any other neurological findings due to MS). The EDSS score ranges from 0 (normal neurological exam) to 10 (death due to MS). EDSS steps 1.0 to 4.5 refer to people with MS who are fully ambulatory. EDSS steps 5.0 to 9.5 are defined by the impairment to ambulation. It is possible for a subject to move in either direction on the scale, for example a worsening of symptoms or relapse is reflected in an increased EDSS score, while an improvement of symptoms or remission is reflected in a decreased EDSS score.

Experimental autoimmune encephalomyelitis (EAE): An animal model of MS (e.g., see Gold et al., *Brain* 129:1953-1971, 2006). EAE exhibits characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS.

Magnetic Resonance Imaging: A noninvasive diagnostic technique that produces computerized images of internal body tissues and is based on nuclear magnetic resonance of atoms within the body induced by the application of radio waves. The MRI techniques for assessing $T_2$-weighted, $T_1$-weighted, Gd-enhanced $T_1$-weighted images, characterization of NAA in the brain have been described (see, for example, Lee et al., *Brain* 122(Pt7):1211-2, 1999; Barkhof and van Walderveen, *Phil. Trans. R. Soc. Lond. B* 354:1675-1686, 1999; Inglese, *Applied Neurology* 3(7) 2007).

$T_2$-weighted brain MM defines lesions with high sensitivity in multiple sclerosis and is used as a measure of disease burden. $T_2$ signal changes can reflect areas of edema, demyelination, gliosis and axonal loss. Areas of gadolinium (Gd) enhancement demonstrated on $T_1$-weighted brain MRI are believed to reflect active perivascular inflammation. Such areas of enhancement are transient, typically lasting <1 month.

Approximately one third of $T_2$-weighted lesions appear hypointense on $T_1$-weighted images ("black holes"). A $T_1$ hypointensity may resolve into an isointense region, suggesting repair, or may persist as a chronic hypointensity. Chronic $T_1$ hypointensities are focal areas of relatively severe tissue injury, including axon injury, matrix destruction, and myelin loss. $T_1$ hypointensities may have a stronger correlation with clinical disability than $T_2$-weighted lesions. $T_1$-weighted images also allow for the assessment of whole brain atrophy.

MRI can be used to characterize tissue metabolites in the brain, including N-acetyl aspartate (NAA), creatine, myo-inositol, lactate, choline, and mobile lipids. NAA is almost exclusively present in neurons and axons and is used as an in vivo marker for axon density or neuronal viability. Decreased levels of NAA are observed in active and established MS lesions.

Mixed lymphocyte reaction (MLR): A method of determining the immunosuppressive activity of a compound. MLR is described e.g. by Meo in "Immunological Methods," L. Lefkovits and B. Devis, Eds, Academic Press N.Y., p. 227-239 (1979) and in U.S. Pat. No. 6,927,208. In this assay, stimulation of proliferation of a mixed lymphocyte culture is measured in the presence or absence of test compounds.

Multiple sclerosis (MS): An autoimmune disease classically described as a CNS white matter disorder disseminated in time and space that presents as relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on $T_2$-weighted and fluid attenuated inversion recovery images, gadolinium enhancement of active lesions, hypointensive "black holes" (representing gliosis and axonal pathology), and brain atrophy on $T_1$-weighted studies. Serial MRI studies can be used to indicate disease progression.

Relapsing-remitting multiple sclerosis is a clinical course of MS that is characterized by clearly defined, acute attacks with full or partial recovery and no disease progression between attacks. Secondary-progressive multiple sclerosis is a clinical course of MS that initially is relapsing-remitting, and then becomes progressive at a variable rate, possibly with an occasional relapse and minor remission. Primary progressive multiple sclerosis presents initially in the progressive form. Clinically isolated syndrome is a first neurologic episode which is caused by inflammation/demyelination at one or more sites in the CNS.

Pharmaceutical agent or drug: A chemical compound capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 15th Edition (1975), describes compositions and formulations suitable for pharmaceutical delivery of the compounds herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In a particular embodiment the carrier is one that allows the therapeutic compound to cross the blood-brain barrier. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween®, sodium acetate or sorbitan monolaurate.

Subject: A human or non-human animal. In one embodiment, the subject has multiple sclerosis.

A subject who has multiple sclerosis who has failed a therapeutic protocol (such as administration of interferon-beta) is a subject who does not respond or fails to respond adequately to the therapy, such that their condition has not improved sufficiently, not changed, or deteriorated in response to treatment with a therapeutically effective amount of the drug. A subject who has failed a therapeutic protocol can require escalating doses of the drug to achieve a desired effect.

Symptom and sign: Any subjective evidence of disease or of a subject's condition, e.g., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with multiple sclerosis.

Therapeutically Effective Amount: A dose sufficient to prevent advancement, delay progression, or to cause regression of the disease, or which is capable of reducing symptoms caused by the disease, such as multiple sclerosis.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety for all purposes. In case of conflict, the present specification, including explanations of terms, will control. In addition, the materials, methods, and examples are illustrative only and not intended to be limiting.

Methods for Treating Subject with Multiple Sclerosis

Methods are provided herein for the treatment of subjects that have multiple sclerosis. In one embodiment the subject has relapsing-remitting multiple sclerosis. In other embodiments, the methods disclosed are used for the treatment of subjects with other forms of multiple sclerosis, such as secondary or primary progressive multiple sclerosis. In several examples, the subject has failed prior therapy with a therapeutic agent. For example, the subject may have been treated with an interferon-beta or another anti-inflammatory agent but did not respond to this therapy.

In the methods disclosed herein, a therapeutically effective amount of a cyclosporin compound described herein is administered to a subject with multiple sclerosis. In some embodiments, the cyclosporin compound is less immunosuppressive than CsA or in some instances non-immunosuppressive. Assays to determine if an agent is immunosuppressive are well known in the art. For example, a mixed lymphocyte reaction (MLR) can be used to assess immunosuppressive activity (see U.S. Pat. No. 6,927,208, incorporated herein by reference). In this assay, stimulation of proliferation of a mixed lymphocyte culture is measured in the presence or absence of test compounds.

In some examples, a compound is less immunosuppressive than CsA if its activity in the MLR is less than CsA, such as about 5-fold less to about 10,000-fold less, for example, about 5-fold less to about 5000-fold less, about 5-fold less to about 2000-fold less, about 5-fold less to about 1000-fold less, about 5-fold less to about 500-fold less, about 10-fold less to about 250-fold less, about 20-fold less to about 100-fold less, or about 25-fold less to about 50-fold less than CsA.

In other examples, other methods of determining if a compound is immunosuppressive may also be used. For example, the ability to reduce cytokine secretion from T lymphocytes is one measure of immunosuppressive activity. The secretion of interleukin-2 (IL-2) from stimulated T cells may be measured by enzyme-linked immunosorbant assay in the presence or absence of test compounds. A compound can be less immunosuppressive than CsA if its inhibition of IL-2 secretion is less than that of CsA, such as about 5-fold less to about 10,000-fold less, for example, about 5-fold less to about 5000-fold less, about 5-fold less to about 2000-fold less, about 5-fold less to about 1000-fold less, about 5-fold less to about 500-fold less, about 10-fold less to about 250-fold less, about 20-fold less to about 100-fold less, or about 25-fold less to about 50-fold less than CsA. Inhibition of secretion of additional cytokines, such as interferon-gamma, interleukin-4, interleukin-5, or interleukin-13 may also be used to assess the immunosuppressive activity of a compound.

In another example, an IL-2 reporter assay may be used to assess immunosuppressive activity (see, e.g. International Publication No. WO 2006/038088). In this assay, T cells are stably transfected with a construct containing a reporter gene, such as β-galactosidase or firefly luciferase, under the control of an IL-2 gene promoter. Following stimulation of the cells in the presence or absence of test compounds, the activity of the reporter gene is monitored. A compound can be less immunosuppressive than CsA if its inhibition of reporter gene activity (such as its $IC_{50}$) is less than CsA, such as about 5-fold less to about 10,000-fold less, for example, about 5-fold less to about 5000-fold less, about 5-fold less to about 2000-fold less, about 5-fold less to about 1000-fold less, about 5-fold less to about 500-fold less, about 10-fold less to about 250-fold less, about 20-fold less to about 100-fold less, or about 25-fold less to about 50-fold less than CsA.

In a further example, immunosuppressive activity may be determined by assessing the proliferative capacity of lymph node cells to cognate antigen in the presence or absence of test compounds (see, e.g., Antoine et al. *Am. J. Pathol.* 148:393-398, 1996; Natarajan and Bright *J. Immunol.* 169:6506-6513, 2002). A compound can be less immunosuppressive than CsA if its inhibition of lymph node cell proliferation is less than CsA, such as about 5-fold less to about 10,000-fold less, for example, about 5-fold less to about 5000-fold less, about 5-fold less to about 2000-fold less, about 5-fold less to about 1000-fold less, about 5-fold less to about 500-fold less, about 10-fold less to about 250-fold less, about 20-fold less to about 100-fold less, or about 25-fold less to about 50-fold less than CsA.

Additional methods of assessing the immunosuppressive activity of compositions are known to one of skill in the art.

In some examples, the cyclosporin compounds described herein inhibit cyclophilin activity (such as CypA or CypD activity). In particular examples, the cyclosporin compounds (such as [D-MeAla]$^3$[EtVal]$^4$-CsA, [MeIle]$^4$-CsA, [MeVal]$^4$-CsA, and [EtPhe(4-CH$_2$PO(OMe)$_2$)]$^4$-CsA) inhibit CypA activity with an apparent $K_i$ that is less than the $K_i$ of CsA (see, e.g., U.S. Pat. No. 6,927,208 and International Publication No. WO 2006/038088).

Methods of assessing cyclophilin activity are known to one skilled in the art. In one example, cyclophilin PPIase activity can be measured based on the preferential cleavage of a substrate peptide (see, e.g. International Publication No. WO 2006/038088). For example, the cis-trans isomerization of the alanine-proline peptide bond in a model substrate, N-succinyl-Ala-Ala-Pro-Phe-4-nitroanilide (SEQ ID NO: 4), may be monitored spectrophotometrically in a coupled assay with chymotrypsin, which releases 4-nitroanilide from the trans form of the substrate. The inhibitory effect upon the addition of different concentrations of inhibitor on the extent of the reaction is determined, and analysis of the change in the first order rate constant as a function of inhibitor concentration yields an estimate of the apparent $K_i$.

In additional examples, the cyclosporin compounds described herein inhibit the mitochondrial permeability transition pore. In particular examples, the cyclosporin compounds (such as [D-MeAla]$^3$[EtVal]$^4$-CsA, [MeIle]$^4$-CsA, and [MeVal]$^4$-CsA) inhibit the mitochondrial permeability transition pore. Assays to measure inhibition of the mitochondrial permeability transition pore (such as analysis of mitochondrial swelling by fluorometric analysis and flow cytometry) are well known to those of skill in the art. See, e.g., Hansson et al., *J. Bioenerg. Biomembr.* 36:407-413, 2004.

In a particular example, the compound or a pharmaceutical composition comprising the compound readily penetrates the blood-brain barrier when peripherally administered. Compounds of this invention which cannot penetrate the blood-brain barrier can be effectively administered by an intraventricular route. In a further example, the pharmaceutical composition comprises a compound of the invention and a pharmaceutically acceptable carrier that allows it to cross the blood-brain barrier.

In some examples, a method of treating multiple sclerosis includes administering a therapeutically effective amount of a cyclosporin having the formula:

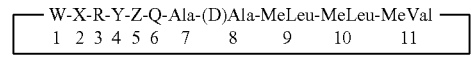

(SEQ ID NO: 1) in which W is MeBmt, dihydro-MeBmt or 8'-hydroxy-MeBmt;
  X is αAbu, Val, Thr, Nva or O-methyl threonine (MeOThr);
  R is Sar, (D)-MeSer, (D)-MeAla, or (D)-MeSer(Oacetyl);
  Y is MeLeu, γ-hydroxy-MeLeu, MeIle, MeVal, MeThr, MeAla, MeaIle or MeaThr; N-EtVal, N-EtIle, N-EtThr, N-Et-Phe, N-EtTyr or N-EtThr(Oacetyl)
  Z is Val, Leu, MeVal or MeLeu; and
  Q is MeLeu, γ-hydroxy-MeLeu or MeAla, wherein the cyclosporin is not cyclosporin A.

The groups W, X, Y, Z, Q and R have, independently, the following preferred significances: W is preferably W' where W' is MeBmt or dihydro-MeBmt; X is preferably X' where X' is αAbu or Nva, more preferably X" where X" is αAbu; R is preferably R' where R' is Sar or (D)-MeAla; Y is preferably Y' where Y' is γ-hydroxy-MeLeu, MeVal, MeThr, MeIle, N-EtIle or N-EtVal; Z is preferably Z' where Z' is Val or MeVal; and Q is preferably Q' where Q' is MeLeu.

In further examples, a method of treating multiple sclerosis includes administering a therapeutically effective amount of a cyclosporin having the formula:

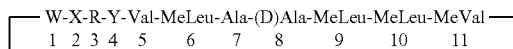

(SEQ ID NO: 2) in which W is -MeBmt or 6,7-dihydro-MeBmt;
  X is -Abu, Nva, Val, or Thr;
  R is Sar, (D)-MeSer, (D)-MeAla, or (D)-MeSer(OAcyl);
  Y is (N—R)aa where aa={Val, Ile, Thr, Phe, Tyr, Thr(OAc), Thr(OG$_1$), Phe(G$_2$), PheCH$_2$(G$_3$), or Tyr(OG$_3$)} with R={alkyl>CH$_3$};
  G$_1$={phenyl-COOH, phenyl-COOMe, or phenyl-COOEt};
  G$_2$={CH$_2$COOH, CH$_2$COOMe(Et)$_4$, CH$_2$PO(OMe)$_2$ or CH$_2$PO(OH)$_2$};
  G$_3$={PO(OH)$_2$, PO(OCH$_2$CH=CH$_2$)$_2$, CH$_2$COOH, CH$_2$COOMe, or CH$_2$COOEt}, wherein the cyclosporin is not cyclosporin A.

Exemplary cyclosporin compounds that may be used in the present invention are those in which W is W', X is X', Y is Y', Z is Z', Q is Q' and R is R'. Examples of specific compounds that may be used include, but are not limited to: [dihydro-MeBmt]$^1$-[γ-hydroxy-MeLeu]$^4$-Cyclosporin; [MeVal]$^4$-Cyclosporin; [MeIle]$^4$-Cyclosporin; [MeThr]$^4$-Cyclosporin; [γ-hydroxy-MeLeu]$^4$-Cyclosporin; [Ethyl-Ile]$^4$-Cyclosporin; [Ethyl-Val]$^4$-Cyclosporin; [Nva]$^2$-[γ-hydroxy-MeLeu]$^4$-Cyclosporin; [γ-hydroxy-MeLeu]$^4$-[γ-hydroxy-MeLeu]$^6$-Cyclosporin; [MeVal]$^5$-Cyclosporin; [MeOThr]$^2$-[(D)MeAla]$^3$-[MeVal]$^5$-Cyclosporin; [8'-hydroxy-MeBmt]$^1$-Cyclosporin; [MeAla]$^6$-Cyclosporin; [γ-hydroxy-MeLeu]$^9$-Cyclosporin; and -[(D)MeAla]$^3$-[EtVal]$^4$-Cyclosporin.

Additional examples of non-immunosuppressive cyclosporins include those described in WO 98/28330, WO 98/28329 and WO 98/28328, each incorporated herein by reference.

In specific embodiments, the cyclosporin is preferably Debio 025 (CAS RN 254435-95-5), which has the chemical name: Cyclo[L-alanyl-D-alanyl-N-methyl-L-leucyl-N-methyl-L-leucyl-N-methyl-L-valyl-(2S,3R,4R,6E)-3-hydroxy-4-methyl-2-methylamino-6-octenoyl-(2S)-2-aminobutanoyl-N-methyl-D-alanyl-N-ethyl-L-valyl-L-valyl-N-methyl-L-leucyl] and has the formula:

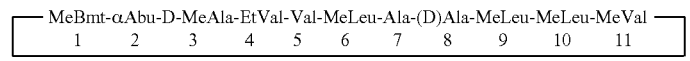

(SEQ ID NO: 5) where MeBmt is N-methyl-(4R)-4-but-2E-en-1-yl-4-methyl-(L)threonine, αAbu is L-α-aminobutyric acid, D-MeAla is N-methyl-D-alanine, EtVal is N-ethyl-L-valine, Val is L-valine, MeLeu is N-methyl-L-leucine, Ala is L-alanine, (D)Ala is D-alanine, and MeVal is N-methyl-L-valine (also designated as [D-MeAla]³[EtVal]⁴-CsA). The conventional numbering of amino acid positions generally used in reference to Cyclosporin A is shown below the formula. This is achieved by using composite names comprising a first portion indicating the identity of residues that are different from those in cyclosporin A and providing their position, and a second portion labeled "CsA" indicating that all other residues are identical to those in Cyclosporin A. For example, [MeIle]⁴-CsA is a cyclosporin that is identical to cyclosporin A except that MeLeu in position 4 is replaced by MeIle (N-methyl-L-isoleucine). In a particular embodiment, the compound is [D-MeAla]³[EtVal]⁴-CsA. Other non-limiting examples include [MeIle]⁴-CsA, [MeVal]⁴-CsA, and [Et-Phe(4-CH₂PO(OMe)₂)]⁴-CsA (see, e.g., U.S. Pat. No. 6,927,208, incorporated herein by reference).

The cyclosporin compounds described herein can be administered parenterally, i.e., subcutaneously, intramuscularly, intraperitoneally, intrathecally, intraventricularly, or intravenously, or by means of a needle-free injection device. Pharmaceutical compositions for parenteral administration for the treatment of MS will commonly include or comprise a compound of formula:

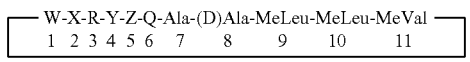

(SEQ ID NO: 1) in which W is MeBmt, dihydro-MeBmt or 8'-hydroxy-MeBmt;

X is αAbu, Val, Thr, Nva or O-methyl threonine (MeOThr);

R is Sar, (D)-MeSer, (D)-MeAla, or (D)-MeSer(Oacetyl);

Y is MeLeu, γ-hydroxy-MeLeu, MeIle, MeVal, MeThr, MeAla, MeaIle or MeaThr; N-EtVal, N-EtIle, N-EtThr, N-Et-Phe, N-EtTyr or N-EtThr(Oacetyl)

Z is Val, Leu, MeVal or MeLeu; and

Q is MeLeu, γ-hydroxy-MeLeu or MeAla, wherein the cyclosporin is not cyclosporin A.

The groups W, X, Y, Z, Q and R have, independently, the following preferred significances: W is preferably W' where W' is MeBmt or dihydro-MeBmt; X is preferably X' where X' is αAbu or Nva, more preferably X" where X" is αAbu; R is preferably R' where R' is Sar or (D)-MeAla; Y is preferably Y' where Y' is γ-hydroxy-MeLeu, MeVal, MeThr, MeIle, N-EtIle or N-EtVal; Z is preferably Z' where Z' is Val or MeVal; and Q is preferably Q' where Q' is MeLeu or, in more particular, a compound of formula:

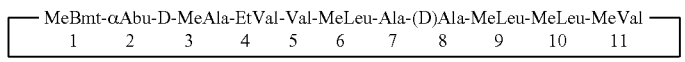

(SEQ ID NO: 5), where MeBmt is N-methyl-(4R)-4-but-2E-en-1-yl-4-methyl-(L)threonine, αAbu is L-α-aminobutyric acid, D-MeAla is N-methyl-D-alanine, EtVal is N-ethyl-L-valine, Val is L-valine, MeLeu is N-methyl-L-leucine, Ala is L-alanine, (D)Ala is D-alanine, and MeVal is N-methyl-L-valine (also designated as [D-MeAla]³[EtVal]⁴-CsA) in a pharmaceutically acceptable carrier as described above. The pharmaceutical composition may also comprise one or more agent or drug as known to be therapeutically active in the treatment of multiple sclerosis. In a further embodiment these agents may be selected from the group consisting of steroid, anti-inflammatory compound, immunosuppressive compound, and antioxidant compound. The pharmaceutical composition may also be administered orally. Additional routes of administration may include sublingual, transdermal, transmucosal, or rectal (e.g. suppository or enema form).

Methods for preparing pharmaceutical compositions are known to those skilled in the art (see Remington's Pharmaceutical Science, 15th ed., Mack Publishing Company, Easton, Pa., 1980). Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. In several embodiments, the composition includes a carrier which allows the cyclosporin compound to cross the blood-brain barrier.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

Pharmaceutical compositions can include pharmaceutically acceptable salts of the disclosed cyclosporin compounds. Pharmaceutically acceptable salts of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found in *Handbook of Pharmaceutical Salts, Properties, Selection and Use*, Wiley VCH (2002).

The cyclosporin compounds described herein can be administered for therapeutic treatment of a subject with multiple sclerosis. Thus, a therapeutically effective amount of a composition comprising the cyclosporin compound is administered to a subject already suffering from MS, in an amount sufficient to improve a sign or a symptom of the disorder. Generally a suitable dose is about 1 milligram per kilogram (mg/kg) to about 50 mg/kg, such as a dose of about 1 mg/kg, about 2 mg/kg, about 5 mg/kg, or about 20 mg/kg administered parenterally. Suitable doses for oral administration are described in Scalfaro et al., US Patent Application Publication No. 2006/0252675, incorporated herein by reference. For example, a suitable dose is about 1 mg/kg to about 100 mg/kg, such as a dose of about 1 mg/kg, about 10 mg/kg, about 20 mg/kg, about 50 mg/kg, or about 100 mg/kg administered orally. Unit dosage forms are also possible, for example 50 mg, 100 mg, 150 mg or 200 mg, or up to 400 mg per dose. However, other higher or lower dosages also could be used, such as from about 0.5 to about 200 mg/kg.

Single or multiple administrations of the composition comprising the cyclosporin compound can be carried out with dose levels and pattern being selected by the treating physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

In one embodiment, the cyclosporin compound is administered without concurrent administration of a second agent for the treatment of MS. In one specific, non-limiting example, [D-MeAla]$^3$-[EtVal]$^4$-CsA is administered without concurrent administration of other agents, such as without concurrent administration of an interferon-beta, such as interferon-beta-1a or interferon-beta-1b. In other specific non-limiting examples, a therapeutically effective amount of [MeIle]$^4$-CsA, [MeVal]$^4$-CsA, or [EtPhe(4-CH$_2$PO(OMe)$_2$)]$^4$-CsA is administered without the concurrent administration of an additional agent.

However, the cyclosporin compound can be administered in combination with a therapeutically effective amount of at least one other agent for the treatment of MS. For example, the cyclosporin compound can be administered with a therapeutically effective amount of a monoclonal antibody, such as daclizumab (ZENAPAX®, U.S. Pat. No. 5,530,101, incorporated herein by reference), natalizumab (TYSABRI®), rituximab (RITUXIN®) or alemtuzumab (CAMPATH®, U.S. Pat. No. 5,545,403). In a further example, the additional agent is an anti-inflammatory agent, such as glatiramer acetate. In an additional example, the additional agent is an anti-oxidant, such as lipoic acid. In another example, the additional agent is a non-cyclosporin inhibitor of cyclophilin D, such as sanglifehrin A or derivatives of sanglifehrin A which have cyclophilin D inhibitory activity (Clarke et al. *J. Biol. Chem.* 277: 34793-34799, 2002). Additional agents also include, but are not limited to, glatiramer acetate (COPAXONE®), inosine, corticosteroids such as prednisone or methylprednisolone; immunosuppressive agents such as cyclosporin (or other calcineurin inhibitors, such as PROGRAF®), azathioprine, sirolimus (RAPAMUNE®), mycophenolate mofetil (CELLCEPT®), laquinimod (ABR-215062), and fingolimod (FTY720); anti-metabolites such as methotrexate; and anti-neoplastic agents such as mitoxantrone. A further additional agent is a combination vaccine against the T cell receptor peptides BV5S2, BV6S5, and BV 13S1 (NEUROVAX®, Darlington *Curr. Opin. Mol. Ther.* 7:598-603, 2005).

In several embodiments, a therapeutically effective amount of a cyclosporin compound and a therapeutically effective amount of interferon beta are administered to a subject with MS. The interferon-beta can be interferon-beta-1a, interferon-beta-1b or a combination thereof. If the interferon-beta is interferon-beta 1b (e.g., BETASERON®), an exemplary dose is 0.25 mg by subcutaneous injection every other day. However, higher or lower doses can be used, for example from 0.006 mg to 2 mg daily, biweekly, weekly, bimonthly or monthly. If the interferon-beta is interferon-beta 1a and is AVONEX®, an exemplary dose is 30 μg injected intramuscularly once a week. However, higher or lower doses could be used, for example 15 to 75 μg daily, biweekly, weekly, bimonthly or monthly. If the interferon-beta 1a is REBIF®, an exemplary dose is 44 μg three times per week by subcutaneous injection. However, higher or lower doses can be used, including treatment daily, biweekly, weekly, bimonthly, or monthly. Additionally, the dosage may be changed during the course of therapy. For example, REBIF® can be administered at an initial dose of 8.8 μg for the first two weeks, then 22 μg for the next two weeks, and then at 44 μg for the rest of the therapy period. In specific embodiments, AVONEX® can be administered at a dose of 30 µg per week or BETASERON® can be administered at a dose of 0.25 mg every other day.

Administration of interferon-beta also can be performed on strict or adjustable schedules. For example, interferon-beta is administered once weekly, every-other-day, or on an adjustable schedule, for example based on concentration in a subject. One of skill in that art will realize that the particular administration schedule will depend on the subject and the dosage being used. The administration schedule can also be different for individual subjects or change during the course of the therapy depending on the subject's reaction. In specific examples, interferon-beta 1a is administered every other week, or monthly.

The combined administration of the cyclosporin compound and interferon-beta includes administering interferon-beta either sequentially with the cyclosporin compound, e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

In one specific, non-limiting example, a therapeutically effective amount of [D-MeAla]$^3$-[EtVal]$^4$-CsA is administered in combination with a therapeutically effective amount of other additional pharmaceutical agents to treat MS. In one example, [D-MeAla]$^3$-[EtVal]$^4$-CsA is administered in combination with interferon-beta, such as interferon-beta-1a or interferon-beta-1b. In further examples, a therapeutically effective amount of [MeIle]$^4$-CsA, [MeVal]$^4$-CsA or [EtPhe(4-CH$_2$PO(OMe)$_2$)]$^4$-CsA are administered in combination with a therapeutically effective amount of other additional pharmaceutical agents, such as anti-inflammatory agents to treat MS. It should be noted that a therapeutically effective amount of more than one of [D-MeAla]$^3$-[EtVal]$^4$-CsA, [MeIle]$^4$-CsA, [MeVal]$^4$-CsA or [EtPhe(4-CH$_2$PO(OMe)$_2$)]$^4$-CsA can be administered to a subject for the treatment of MS, such as primary progressive or secondary progressive MS.

The combined administration of the cyclosporin compound and additional pharmaceutical agents includes administering the additional agent either sequentially with the cyclosporin compound, e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

In several examples, the cyclosporin compound is administered to a subject with relapsing-remitting MS, primary progressive MS, or secondary progressive MS. In a particular example, the cyclosporin compound is administered to a subject during a relapse phase, for example to promote recovery. In a non-limiting example, the cyclosporin compound is administered in combination with an anti-inflammatory agent, such as glatiramer acetate.

Treatment with a cyclosporin compound described herein, alone or in combination with other agents, will reduce the severity of disease. In one example, the severity of the disease is reduced by at least about 25%, such as about 50%, about 75%, or about 90% reduction. In another example, treatment with a cyclosporin compound will reduce white matter tissue damage by at least about 30%, such as about 40%, about 50%, about 70%, or about 80%. In a further example, treatment with a cyclosporin compound will reduce axon loss by at least about 30%, such as about 50%, about 60%, about 70%, or about 80%. In another example, treatment with a cyclosporin compound will promote repair of axon damage by at least about 25% improvement, such as about 30%, about 40%, or about 50% improvement.

Treatment with a cyclosporin compound, alone or in combination with other agents, will decrease MRI measures of MS. In several embodiments, the administration of the cyclophilin inhibitor results in stabilization of the number of black holes on an MM and/or stabilization of the number of $T_2$-weighted lesions and/or an increase in NAA following administration of the cyclosporin compound. In one example, the number of $T_2$-weighted lesions will decrease by at least about 10%, such as about 20%, about 30%, about 50% or about 70%. In a further example, treatment with a cyclosporin compound will decrease $T_1$-weighted hypointense regions. In a particular example, the $T_1$ hypointense regions will decrease in number by at least about 10%, such as about 20%, about 30%, about 50% or about 70%. In an additional particular example, the $T_1$ hypointense regions will decrease in volume by at least about 10%, such as about 20%, about 30%, about 50% or about 70%. In another example, NAA levels will increase by at least about 10%, such as about 20%, about 30%, or about 40%.

In several embodiments, treatment with the cyclosporin compound described herein, alone or in combination with other agents, will reduce the average number of MS exacerbations per subject in a given period (such as 6, 12, 18 or 24 months) by at least about 25%, such as at least about 40% or at least about 50%, as compared to a control. In one embodiment, the number of MS exacerbations is reduced by at least about 80%, such as at least about 90%, as compared to control subjects. The control subjects can be untreated subjects or subjects not receiving the cyclosporin compound (e.g., subjects receiving other agents).

Treatment with the cyclosporin compound, alone or in combination with other agents, can also reduce the average rate of increase in the subject's disability score over some period (e.g., 6, 12, 18 or 24 months), e.g., as measured by the EDSS score, by at least about 10% or about 20%, such as by at least about 30%, 40% or 50%. In one embodiment, the reduction in the average rate of increase in the EDSS score is at least about 60%, at least about 75%, or at least about 90% compared to control subjects, such as untreated subjects or subjects not receiving the cyclosporin compound but possibly receiving other agents. In another embodiment, treatment with a cyclosporin compound will prevent decline in the subject's EDSS score. In a further embodiment, the subject's EDSS score will improve, by at least about 10% or about 20%, such as by at least about 30%, 40% or 50% compared to control subjects, such as untreated subjects or subjects not receiving the cyclosporin compound but possibly receiving other agents. These benefits can be demonstrated in one or more randomized, placebo-controlled, double-blinded, Phase II or III clinical trials and will be statistically significant (e.g., $p<0.05$).

The present disclosure is illustrated by the following non-limiting Examples.

EXAMPLES

MS has become increasingly viewed as a neuron degenerative disorder, in which neuronal loss, axonal injury, and atrophy of the brain occurs progressively from the start of the disease. Permanent neurological and clinical disability, especially in patients of long disease duration, is thought to develop when a threshold of axonal loss is reached, and CNS compensatory responses are exhausted. Progressive axonal loss in MS may stem from a cascade of ionic imbalances initiated by inflammation, leading to mitochondrial dysfunction and energetic deficits that result in mitochondrial and cellular $Ca^{2+}$ overload. Mice lacking expression of mitochondrial cyclophilin D, a key regulator of mitochondrial $Ca^{2+}$ homeostasis, are resistant to the induction of experimental autoimmune encephalomyelitis and are able to recover clinically (Forte et al. *Proc. Natl. Acad. Sci. USA* 104:7558-7563, 2007). This suggests a direct link between mitochondrial function, $Ca^{2+}$ overload and axonal destruction during EAE, and by extension, MS.

Example 1

Assessment of the Immunosuppressive Effect of [D-MeAla]$^3$-[EtVal]$^4$-CsA

This example describes the assessment of [D-MeAla]$^3$-[EtVal]$^4$-CsA for immunosuppressive effects in vitro and in an in vivo mouse model of MS.

Female C57BL/6 (B6) mice were immunized with MOG 35-55 peptide in complete Freund's adjuvant containing 400 µg of *Mycobacterium tuberculosis* per mouse by subcutaneous injection. Pertussis toxin was administered intraperitoneally at day 0 (25 ng per mouse) and day 2 (66 ng per mouse) after immunization. Ten days later inguinal lymph nodes were harvested, pooled, and single cell suspensions were generated. After 48 hours, cells were pulsed with [$^3$H]thymidine and harvested 18 hours later to assess proliferation. Triplicate wells of lymph node cells were treated with 25 µg/ml MOG 35-55 peptide in the presence or absence of [D-MeAla]$^3$-[EtVal]$^4$-CsA and CsA, and their respective vehicles.

In B6 mice, [D-MeAla]$^3$-[EtVal]$^4$-CsA does not suppress lymphocyte proliferation to MOG 35-55 peptide, while CsA does. The presence of [D-MeAla]$^3$-[EtVal]$^4$-CsA did not significantly alter the proliferative capacity of lymph node cells as compared to MOG 35-55 peptide alone (FIG. 1), indicating its lack of immunosuppressive effect. However, equimolar concentrations of CsA significantly inhibited MOG 35-55 peptide stimulated lymph node cell proliferation.

In addition, B6 mice were immunized with MOG 35-55 peptide and then given either no treatment, [D-MeAla]$^3$-[EtVal]$^4$-CsA at 20 mg/kg/day, or vehicle. Splenocytes or lymphocytes from mice treated with [D-MeAla]$^3$-[EtVal]$^4$-CsA or vehicle showed no differences in proliferation in response to MOG 35-55 peptide, indicating that [D-MeAla]$^3$-[EtVal]$^4$-CsA was not immunosuppressive in vivo.

Example 2

Clinical Course of EAE in Mice Treated with [D-MeAla]$^3$-[EtVal]$^4$-CsA

This example describes the ability of varying doses of [D-MeAla]$^3$-[EtVal]$^4$-CsA to suppress the clinical course of EAE in mice when treatment begins prior to disease onset.

EAE was induced in C57BL/6 (B6) female mice by immunization with 200 µg of MOG 35-55 peptide in complete Freund's adjuvant containing 400 µg of *Mycobacterium tuberculosis* per mouse by subcutaneous injection. Pertussis toxin was administered intraperitoneally at day 0 (25 ng per mouse) and day 2 (66 ng per mouse) after immunization. Ten days after immunization, animals were randomized into four groups (4 mice per group) that received daily injections of [D-MeAla]$^3$-[EtVal]$^4$-CsA in one of three doses (1 mg/kg, 5 mg/kg, or 20 mg/kg) or daily injections of vehicle. Mice were examined for signs of EAE daily, blinded to treatment status. EAE was scored by using a 9 point scale (0, no paralysis; 1, limp tail with minimal hind limb weakness; 2, mild hind limb weakness; 3, moderate hind limb weakness; 4, moderately severe hind limb weakness; 5, severe hind limb weakness; 6, complete hind limb paralysis; 7, hind limb paralysis with mild forelimb weakness; 8, hind limb paralysis with moderate forelimb weakness; and 9, hind limb paralysis with severe forelimb weakness).

Figure 2:
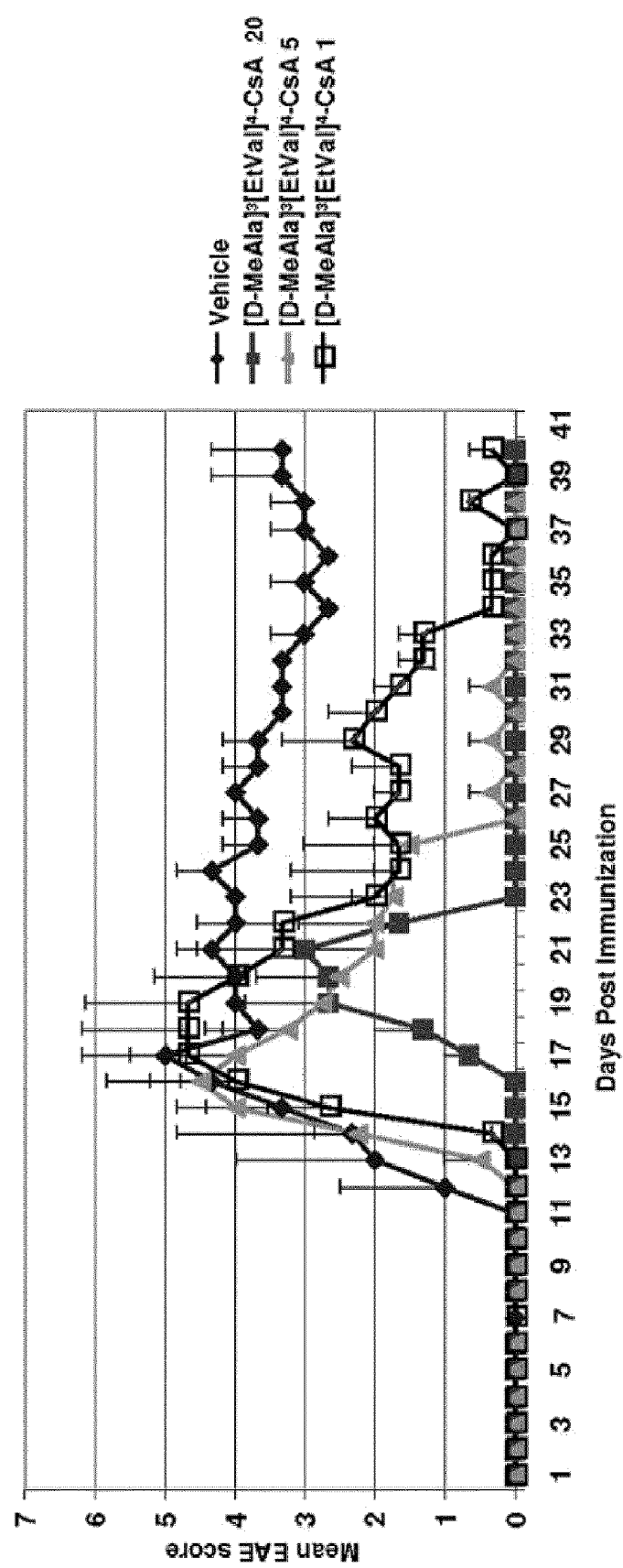
FIG. 2 is a schematic diagram showing the mean EAE score for C57BL/6 mice immunized with MOG 35-55 peptide to induce EAE and treated prior to disease onset (starting at day 10) with vehicle (diamond) or daily injection of 1 mg/kg [D-MeAla]$^3$[EtVal]$^4$-CsA (closed square), 5 mg/kg [D-MeAla]$^3$[EtVal]$^4$-CsA (triangle), or 20 mg/kg [D-MeAla]$^3$[EtVal]$^4$-CsA (open square). Error bars indicate standard error of the mean.

Beginning on day 12, mice receiving vehicle developed clinical EAE and followed a typical course for B6 mice. Mice receiving [D-MeAla]$^3$-[EtVal]$^4$-CsA had less severe EAE at all doses over the course of the experiment and there was a clear dose response (FIG. 2). In mice receiving the highest dose (20 mg/kg), the onset of disease was significantly delayed and severity of peak disease was reduced when compared to vehicle treated mice (FIG. 2). In addition, all [D-MeAla]$^3$-[EtVal]$^4$-CsA treated mice, even at the lowest doses, completely recovered over the course of the experiment, in contrast to vehicle treated mice (FIG. 2). At the end of the experiment, the mean total EAE score for the vehicle control group was 99, while the mean total EAE scores for the groups treated with 1, 5, and 20 mg/kg/day of [D-MeAla]$^3$-[EtVal]$^4$-CsA were 53, 25, and 12, respectively.

Example 3

Reversal of Paralysis in EAE Mice Treated with [D-MeAla]$^3$-[EtVal]$^4$-CsA

This example describes the effect of treatment with [D-MeAla]$^3$-[EtVal]$^4$-CsA on paralysis in mice with EAE.

EAE was induced in B6 mice as described in Example 2. Mice developed signs of EAE 10-12 days following immunization with MOG 35-55 peptide. On day 15, after onset of paralysis, mice were randomized into two groups (12 mice per group), with one group receiving daily injections of [D-MeAla]$^3$-[EtVal]$^4$-CsA (20 mg/kg) and the other group receiving daily injections of vehicle. Mice were scored daily for EAE, blinded to treatment status.

Figure 3:
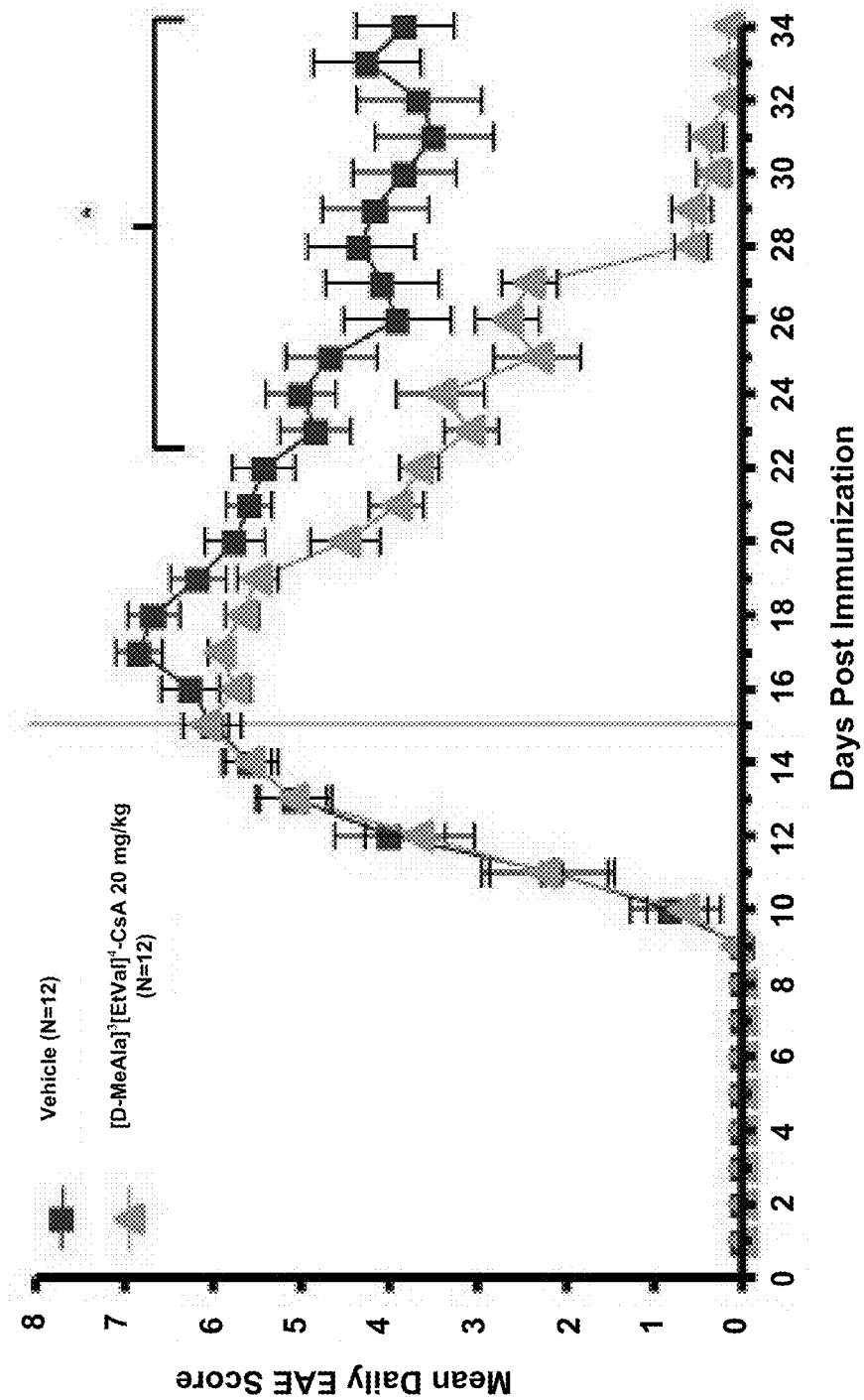
FIG. 3 is a schematic diagram showing the mean daily EAE score for C57BL/6 mice immunized with MOG 35-55 peptide to induce EAE and treated with daily injection of vehicle (square) or 20 mg/kg [D-MeAla]$^3$[EtVal]$^4$-CsA (triangle) beginning on day 15 post-immunization. The daily cumulative EAE scores were calculated and statistical significance between the vehicle and [D-MeAla]$^3$[EtVal]$^4$-CsA treated groups was determined with the Mann Whitney U test. * denotes a statistically significant difference of p<0.05.

Mice receiving vehicle showed some clinical improvement. However, mice treated with [D-MeAla]$^3$-[EtVal]$^4$-CsA showed progressive improvement, eventually returning to nearly normal (FIG. 3). The differences between vehicle and [D-MeAla]$^3$-[EtVal]$^4$-CsA treated mice became statistically significant commencing on day 22. At the conclusion of the study, the mean total EAE score of the vehicle treated group was 116, while the [D-MeAla]$^3$-[EtVal]$^4$-CsA treated mice had a mean total EAE score of 75 (p=0.0006). Thus, [D-MeAla]$^3$-[EtVal]$^4$-CsA was able to effectively reverse paralysis in mice with EAE when therapy was started after the onset of disease.

Example 4

In vivo Neuroprotective Effects of [D-MeAla]$^3$-[EtVal]$^4$-CsA in Mice with EAE This example describes the in vivo neuroprotective effects of [D-MeAla]$^3$-[EtVal]$^4$-CsA in EAE in mice. Neuroprotection is assessed by white matter tissue damage and presence of phosphorylated neurofilaments (NF-P).

White Matter Tissue Damage

Mice with induced EAE were deeply anesthetized with isoflurane, heparinized, and perfused with 5% gluteraldehyde, and spinal cords were dissected as described in Masliah et al., *Am. J. Pathol.* 142:871-882, 1993. Tissue samples were post-fixed with 1% osmium. Semithin sections (0.5 μm) were stained with toluidine blue and photographed at 25× magnification. The percentage of the spinal cord showing damage was determined in the ventrolateral and dorsal thoracic cord. Photomontages (final magnification 100×) of the entire spinal cord and areas containing damaged fibers were measured using a SummaSketch 111 (Summagraphics, Fairfield, Conn.) digitizing tablet and BIOQUANT Classic 95 software (R & M Biometrics, Nashville, Tenn.). Measurements were taken of the total area (damaged and nondamaged) and the cumulative percentage area of lesions was calculated.

Figure 4E:
FIG. 4 shows photomicrographs of thoracic spinal cord sections of the ventrolateral white matter stained with toluidine blue from (A) naïve mouse, (B) mouse with EAE treated with vehicle alone, (C) mouse with EAE treated with 1 mg/kg/day of [D-MeAla]$^3$[EtVal]$^4$-CsA, (D) mouse with EAE treated with 5 mg/kg/day of [D-MeAla]$^3$[EtVal]$^4$-CsA, (E) mouse with EAE treated with 20 mg/kg/day of [D-MeAla]$^3$[EtVal]$^4$-CsA. Arrows indicate fibers undergoing Wallerian-like degeneration. Bar=250 µm.

Thoracic spinal cords of mice receiving $[D-MeAla]^3$-$[EtVal]^4$-CsA displayed a dose-dependent reduction in white matter tissue damage compared with those of mice receiving vehicle (FIG. 4). The greatest reductions occurred in mice receiving the highest dose of $[D-MeAla]^3$-$[EtVal]^4$-CsA. In the ventrolateral thoracic cord, $[D-MeAla]^3$-$[EtVal]^4$-CsA at doses of 1, 5, and 20 mg/kg/day reduced tissue damage by 40%, 76%, and 86%, respectively. In the dorsal thoracic cord, these doses of $[D-MeAla]^3$-$[EtVal]^4$-CsA reduced tissue damage by 50%, 69%, and 81%, respectively.

Phosphorylated Neurofilaments

Mice with induced EAE were perfused with 4% paraformaldehyde and 1- to 2-mm lengths of spinal cord were processed for sectioning as described in Masliah et al. Spinal cord sections were blocked and stained with anti-phosphorylated NF, SMI312 (Sternberger Monoclonals, Lutherville, Md.). Following incubation in goat anti-mouse secondary antibody and incubation in mouse peroxidase-antiperoxidase, immunoreactivity was visualized with 0.05% diaminobenzidine tetrahydrochloride/0.01% hydrogen peroxide, examined by light microscopy and photographed and analyzed as described for assessing white matter tissue damage. Statistical significance was determined by using one-way ANOVA followed by Newman-Keuls multiple comparisons tests (WINKS 4.62 professional edition; Texasoft, Dallas, Tex.); significance was defined as $p<0.05$.

Loss of immunohistochemical staining for NF-P reflects both degeneration and loss of axons, and also presence of axons in which there has been NF dephosphorylation in response to injury. Thus, measurement of changes in immunostaining for phosphorylated NF gives a measure of axonal loss and injury. $[D-MeAla]^3$-$[EtVal]^4$-CsA treated mice had significant preservation of NF-P by immunohistochemical staining compared with vehicle treated mice (FIG. 5). In the lateral/ventral thoracic spinal cord, $[D-MeAla]^3$-$[EtVal]^4$-CsA at doses of 1, 5, and 20 mg/kg demonstrated a mean area of loss of NF-P staining of 14.5%, 3%, and 1.5% respectively, compared to a reduction of 24% in the spinal cord of vehicle-treated mice.

Example 5

Repair of Injured Axons Following Treatment with $[D-MeAla]^3$-$[EtVal]^4$-CsA in Mice with EAE This example describes the in vivo promotion of repair of injured axons in a mouse EAE model by treatment with $[D-MeAla]^3$-$[EtVal]^4$-CsA.

B6 mice were immunized with MOG 35-55 peptide as described in Example 2. At day 15, when mice had developed paralysis, mice were randomized into one of three groups: one group was perfused and their spinal cords processed for immunostaining for NF-P as described in Example 4; one group received daily injections of 20 mg/kg $[D-MeAla]^3$-$[EtVal]^4$-CsA; one group received daily injections of vehicle. The two treatment groups were perfused on day 40 post-immunization and sections of their spinal cords were immunostained for NF-P.

Figure 6A:
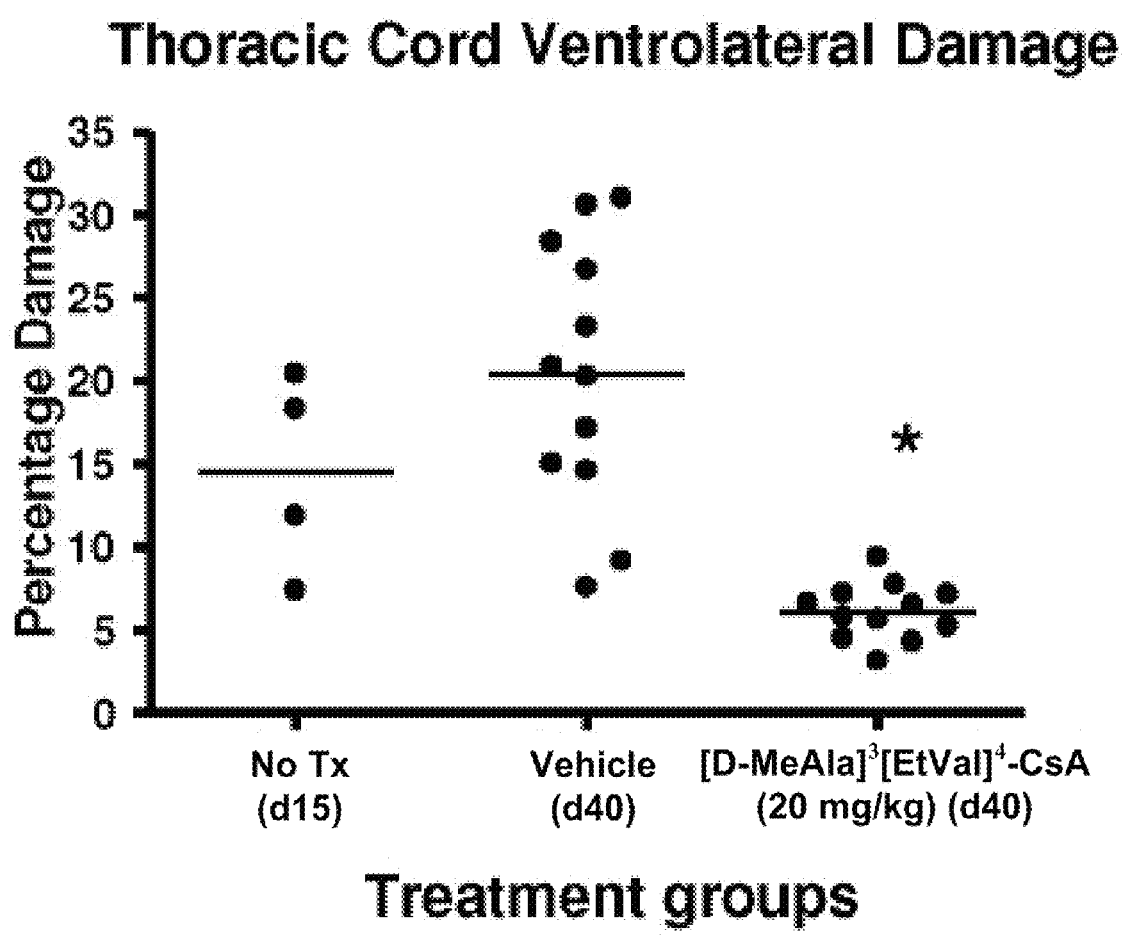
FIG. 6A shows percentage of area of axon damage in ventrolateral white matter.
Figure 6B:
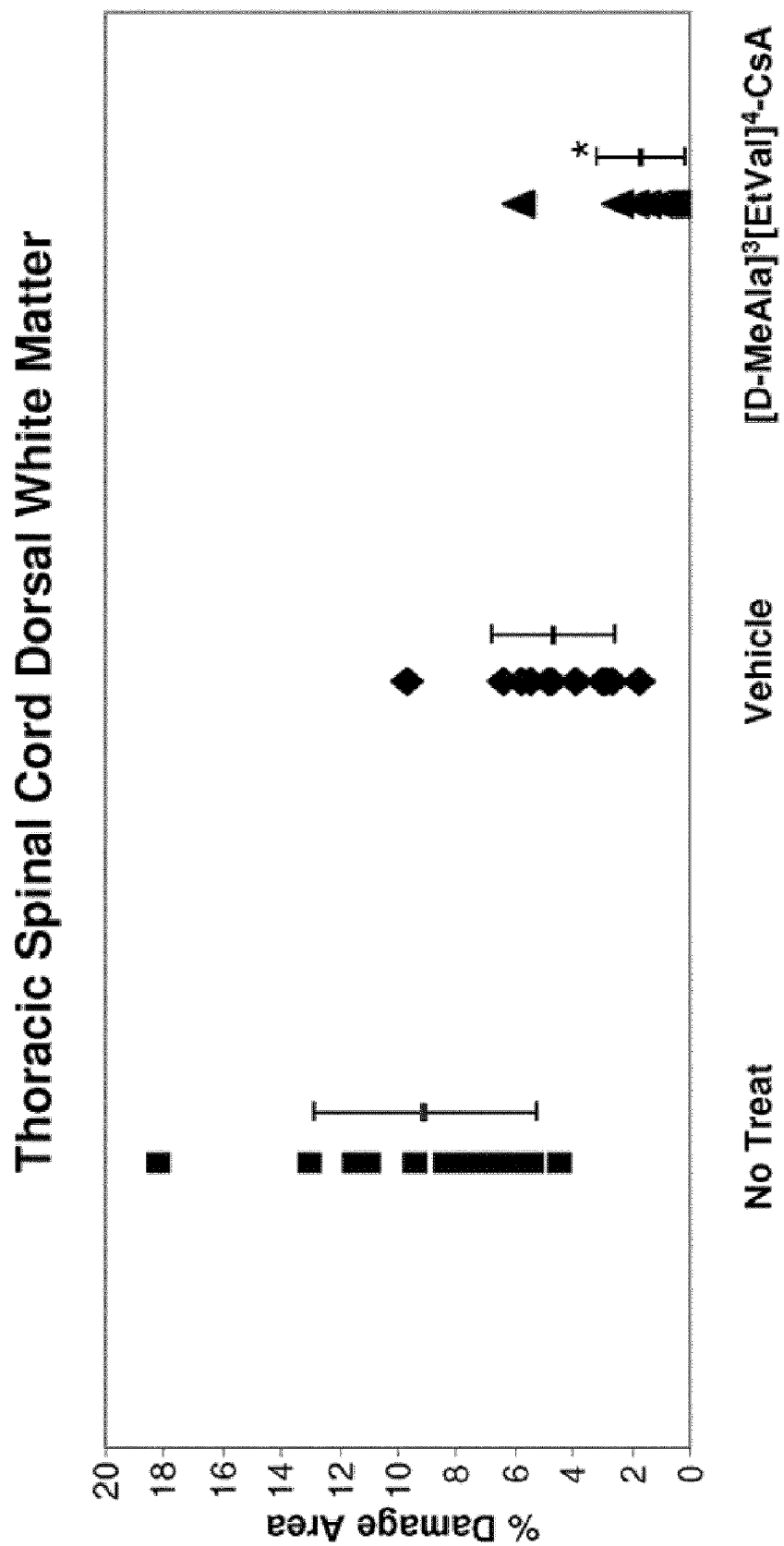
FIG. 6B shows percentage of area of axon damage in dorsal white matter. * denotes a p value <0.001 between vehicle and [D-MeAla]$^3$[EtVal]$^4$-CsA treatment groups.

The spinal cord sections from mice perfused at day 15 after immunization with MOG 35-55 peptide showed that 14% of the ventrolateral spinal cord white matter had reduced staining for NF-P (FIG. 6A). Spinal cord sections from mice treated with $[D-MeAla]^3$-$[EtVal]^4$-CsA had reduced NF-P staining in only 7% of the ventrolateral spinal cord at day 40 after immunization with MOG 35-55 peptide (FIG. 6A). Vehicle treated mice had reduced NF-P staining in 20% of the ventrolateral spinal cord (FIG. 6A). Similarly, spinal cord sections from mice perfused at day 15 after immunization with MOG 33-55 peptide had 9% reduction in NF-P staining in the dorsal spinal cord, while spinal cord sections from mice treated with $[D-MeAla]^3$-$[EtVal]^4$-CsA had reduced NF-P staining in only 1.7% of the dorsal spinal cord at day 40 (FIG. 6B). Vehicle treated mice had reduced NF-P staining in 4.7% of the dorsal spinal cord (FIG. 6B). Therefore, treatment with $[D-MeAla]^3$-$[EtVal]^4$-CsA not only prevented increased axonal damage, but also promoted repair, with at least a 50% improvement in expression of NF-P within axons.

Example 6

Immune and Inflammatory Response to $[D-MeAla]^3$-$[EtVal]^4$-CsA in an In Vivo Mouse Model This example describes assessment of the immune and inflammatory response to $[D-MeAla]^3$-$[EtVal]^4$-CsA in a mouse EAE model.

EAE was induced in C57BL/6 mice by immunization with MOG 33-55 as described in Example 2. Mice were randomized into three groups (no treatment, vehicle control, and 20 mg/kg/day $[D-MeAla]^3$-$[EtVal]^4$-CsA) on day 15 at peak disease. Mice received therapy by daily subcutaneous injection. Mice were euthanized at day 34 to 40 post-immunization by perfusion with 4% paraformaldehyde and spinal cords were removed for immunohistochemical staining and quantitative analysis. Spinal cord sections were stained with anti-CD4 (lymphocyte) or anti-CD11b (monocyte/macrophage lineage) antibodies and quantified following image capture on a laser scanning confocal microscope.

Figure 7:
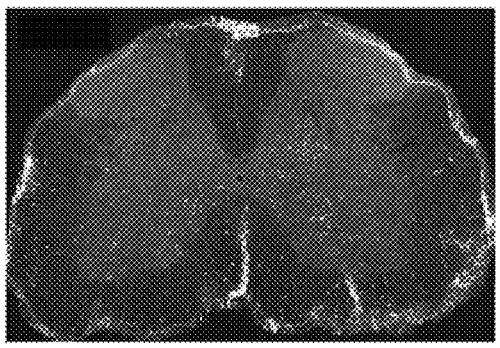
FIG. 7 shows photomicrographs of lumbar spinal cord sections from C57BL/6 mice immunostained for CD4 from an EAE mouse with no treatment (No TX), an EAE mouse treated with vehicle alone (VC), a mouse with EAE treated with 20 mg/kg/day of [D-MeAla]$^3$[EtVal]$^4$-CsA at 34-40 days after immunization with MOG 35-55, and a naïve mouse.
Figure 7:
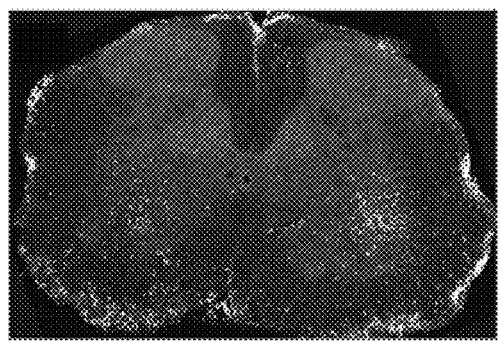
Figure 7:
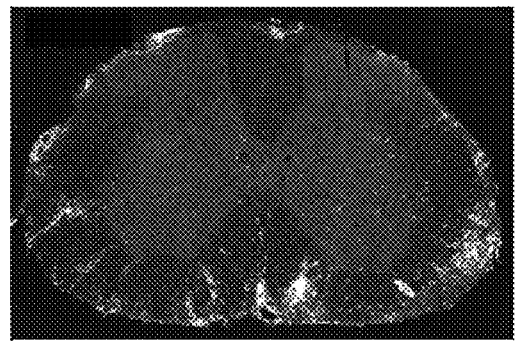
Figure 7:
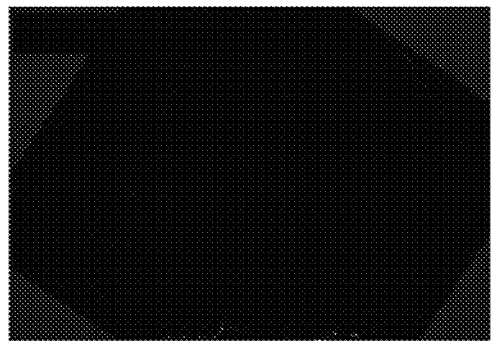
Figure 8:
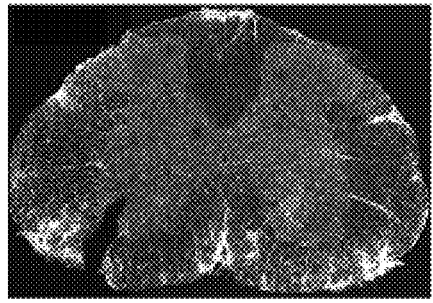
FIG. 8 shows photomicrographs of lumbar spinal cord sections from C57BL/6 mice immunostained for CD11b from an EAE mouse with no treatment (No TX), an EAE mouse treated with vehicle alone (VC), a mouse with EAE treated with 20 mg/kg/day of [D-MeAla]$^3$[EtVal]$^4$-CsA at 34-40 days after immunization with MOG 35-55, and a naïve mouse.
Figure 8:
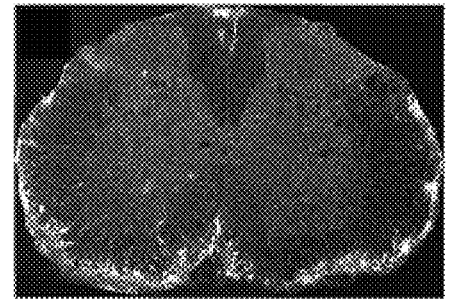
Figure 8:
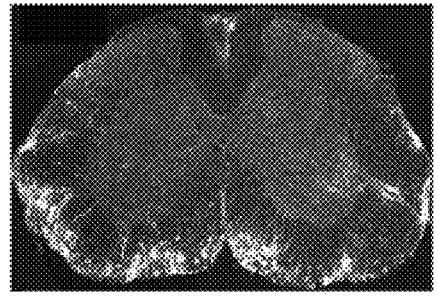
Figure 8:
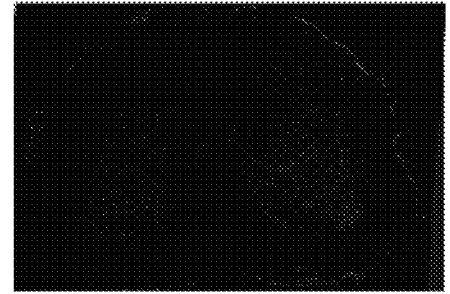
Figure 9:
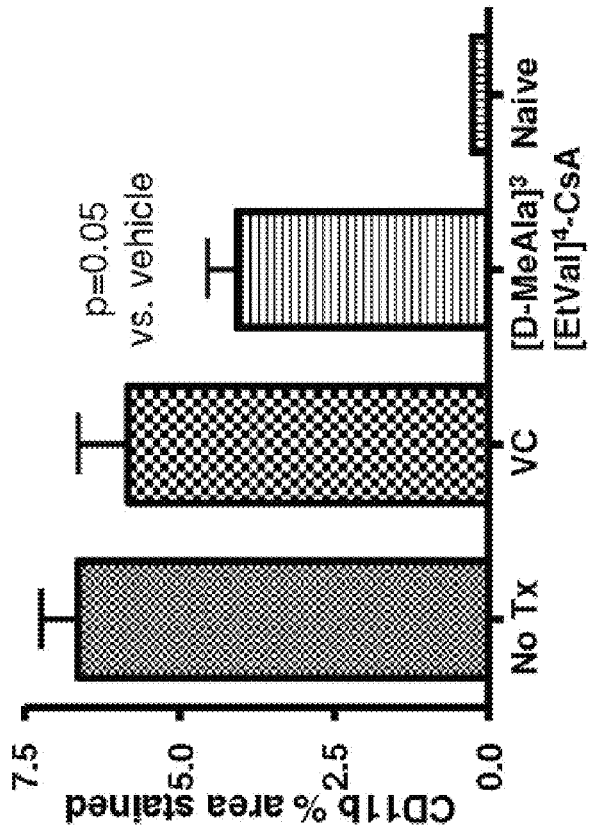
Figure 9:
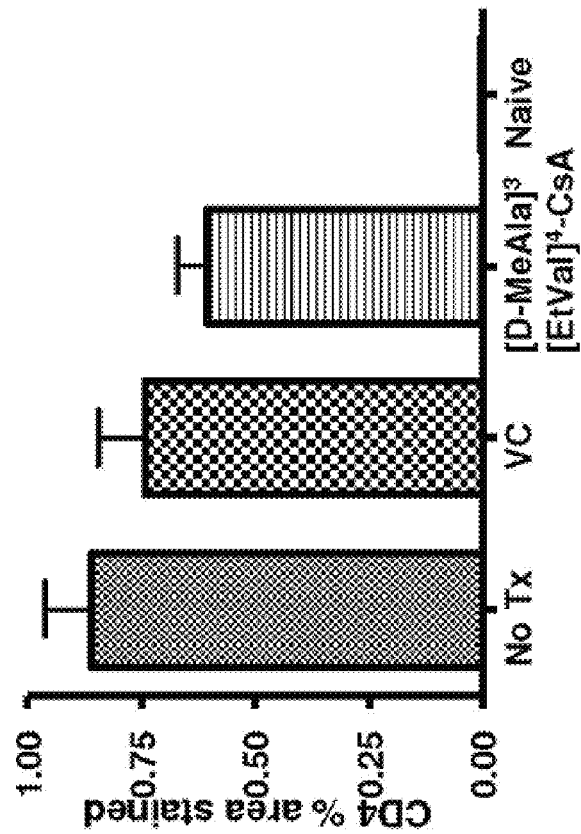

Induction of EAE resulted in the presence of inflammatory infiltrates in the spinal cord. CD4 positive and CD11b positive cells infiltrated the spinal cord following induction of EAE by immunization with MOG 33-55 peptide. The percentage area stained by anti-CD4 was 0.86%, 0.74%, and 0.61% in spinal cords from no treatment, vehicle control, and $[D-MeAla]^3$-$[EtVal]^4$-CsA-treated mice, respectively (FIGS. 7 and 9). Differences in CD4 among the groups were not significant. CD11b cells were present in 6.64%, 5.83%, and 3.94% of the white matter from no treatment, vehicle control, and $[D-MeAla]^3$-$[EtVal]^4$-CsA-treated mice, respectively (FIGS. 8 and 9). Differences among EAE groups for CD11b were somewhat significant: $[D-MeAla]^3$-$[EtVal]^4$-CsA vs. vehicle $p=0.05$; $[D-MeAla]^3$-$[EtVal]^4$-CsA vs. no treatment $p=0.007$. In contrast, naïve mice (not immunized with MOG 33-55 peptide) had areas of 0.005% and 0.26% stained by anti-CD4 and anti-CD11b, respectively.

Example 7

Assessment of the Efficacy of Cyclosporin Compounds for the Treatment of Multiple Sclerosis This example describes methods for the assessment of the efficacy of the use of the cyclosporin compounds described herein for the treatment of MS.

Subjects having multiple sclerosis are treated daily with a cyclosporin compound, for example, $[\text{D-MeAla}]^3$-$[\text{EtVal}]^4$-CsA or other cyclosporin compounds described herein, at doses of 1 mg/kg to 25 mg/kg. Subjects are assessed for measures of MS described below prior to initiation of therapy, periodically during the period of therapy and at the end of the course of treatment.

The efficacy of cyclosporin compound therapy in subjects with multiple sclerosis can be assessed by the following measures:

1. MRI measures, such as
    $T_2$ lesion load,
    Volume of $T_1$ hypointensities,
    NAA levels,
    Whole brain atrophy;
2. Clinical measures, specifically,
    Change in EDSS, change in SRS (Scripps Neurological Rating Scale)
    Relapse rate; 9-hole peg test
3. Immunologic measures, specifically,
    Markers of Th1 and Th2 T cell lineages, as well as FACS analysis of various T cell markers,
    Cytokine production by T cells in vitro,
    Proliferation of T cells $T_2$ Lesion Load The analyses on $T_2$ lesion load include the following:
comparison of the mean volume of $T_2$ lesions during the pre-treatment period to the mean volume of $T_2$ lesions during the treatment period
comparison of the mean volume of $T_2$ lesions during the pre-treatment period to the mean volume of $T_2$ lesions during the last 4 weeks of the treatment period Volume of $T_1$ Hypointensities The analyses on volume of $T_1$ hypointensities include the following:
comparison of the mean volume of $T_1$ hypointensities during the pre-treatment period to the mean volume of $T_1$ hypointensities during the treatment period
comparison of the mean volume of $T_1$ hypointensities during the pre-treatment period to the mean volume of $T_1$ hypointensities during the last 4 weeks of the treatment period

EDSS

Baseline EDSS score is determined for subjects prior to start of treatment. EDSS is measured periodically during the course of treatment. The change from baseline EDSS to EDSS during the treatment period is determined. Also, change from baseline scores for SRS and the 9-hole peg test during the treatment period are determined.

Relapses

The frequency of relapses over the 2 years prior to receiving study drug are compared to the frequency of relapses on study drug.

The effectiveness of cyclosporin compound therapy in subjects with MS can be demonstrated by a reduction in the average number of MS exacerbations per subject in a given period (such as 6, 12, 18 or 24 months) compared with a period prior to treatment. A reduction in the average rate of increase in the subject's disability score over some period (e.g., 6, 12, 18 or 24 months), e.g., as measured by the EDSS score, or even an improvement in the disability score, can also demonstrate the effectiveness of cyclophilin inhibitor therapy.

In view of the many possible embodiments to which the principles of the disclosure may be applied, it should be recognized that the illustrated embodiments are only preferred examples and should not be taken as limiting the scope of the invention. Rather, the scope of the invention is defined by the following claims. We therefore claim as our invention all that comes within the scope and spirit of these claims.

---

We claim:

1. A method for treating a subject with multiple sclerosis, comprising administering to the subject a therapeutically effective amount of Cyclo[L-alanyl-D-alanyl-N-methyl-L-leucyl-N-methyl-L-leucyl-N-methyl-L-valyl-(2S,3R,4R,6E)-3-hydroxy-4-methyl-2-methylamino-6-octenoyl-(2S)-2-aminobutanoyl-N-methyl-D-alanyl-N-ethyl-L-valyl-L-valyl-N-methyl-L-leucyl].

2. The method of claim 1, wherein the multiple sclerosis comprises relapsing-remitting multiple sclerosis, secondary progressive multiple sclerosis, primary progressive multiple sclerosis, or clinically isolated syndrome.

3. The method of claim 1, wherein ameliorating a symptom of multiple sclerosis comprises decreasing axon damage.

4. The method of claim 1, wherein ameliorating a symptom of multiple sclerosis comprises repair of axon damage.

5. The method of claim 1, further comprising administering to the subject a therapeutically effective amount of a second agent for the treatment of multiple sclerosis.

6. The method of claim 5, wherein the second agent for the treatment of multiple sclerosis is selected from the group consisting of a steroid, an anti-inflammatory compound, an immunosuppressive compound, and an antioxidant.

7. The method of claim 6, wherein the second agent is beta-interferon.

8. The method of claim 6, wherein the second agent is glatiramer acetate.

9. The method of claim 6, wherein the second agent is lipoic acid.

10. The method of claim 5, wherein the second agent is a monoclonal antibody.

11. The method of claim 10, wherein the monoclonal antibody is selected from the group consisting of daclizumab, rituximab and natalizumab.

12. The method of claim 5, wherein the second agent is sanglifehrin A or a derivative of sanglifehrin A.

* * * * *